US010513505B2

(12) United States Patent
Wirth et al.

(10) Patent No.: US 10,513,505 B2
(45) Date of Patent: Dec. 24, 2019

(54) ANTIFUNGAL COMPOUND PROCESS

(71) Applicant: NQP 1598, LTD., Grand Cayman (KY)

(72) Inventors: David Dale Wirth, Oak Ridge, NC (US); Christopher M. Yates, Raleigh, NC (US); William J. Hoekstra, Durham, NC (US)

(73) Assignee: NQP 1598, LTD., Grand Cayman (KY)

( * ) Notice: Subject to any disclaimer, the term of this patent is extended or adjusted under 35 U.S.C. 154(b) by 0 days.

(21) Appl. No.: 15/760,812

(22) PCT Filed: Sep. 16, 2016

(86) PCT No.: PCT/US2016/052151
§ 371 (c)(1),
(2) Date: Mar. 16, 2018

(87) PCT Pub. No.: WO2017/049096
PCT Pub. Date: Mar. 23, 2017

(65) Prior Publication Data
US 2018/0258068 A1 Sep. 13, 2018

Related U.S. Application Data

(60) Provisional application No. 62/275,504, filed on Jan. 6, 2016, provisional application No. 62/220,384, filed on Sep. 18, 2015.

(51) Int. Cl.
| | | |
|---|---|---|
| C07D 401/06 | (2006.01) |
| C07D 453/02 | (2006.01) |
| C07D 213/30 | (2006.01) |
| C07C 303/44 | (2006.01) |
| C07C 309/30 | (2006.01) |

(52) U.S. Cl.
CPC .......... *C07D 401/06* (2013.01); *C07C 303/44* (2013.01); *C07C 309/30* (2013.01); *C07D 213/30* (2013.01); *C07D 453/02* (2013.01); *C07B 2200/13* (2013.01)

(58) Field of Classification Search
CPC .................................................. C07D 401/06
USPC ....................................... 546/268.4; 514/340
See application file for complete search history.

(56) References Cited

U.S. PATENT DOCUMENTS

| | | |
|---|---|---|
| 4,404,216 A | 9/1983 | Richardson et al. |
| 4,616,026 A | 10/1986 | Richardson et al. |
| 8,883,797 B2 | 11/2014 | Hoekstra et al. |
| 9,309,273 B2 | 4/2016 | Hoekstra et al. |
| 2005/0209259 A1 | 9/2005 | Huang |
| 2009/0306066 A1 | 12/2009 | Qin et al. |
| 2012/0329802 A1 | 12/2012 | Hoekstra et al. |
| 2013/0005719 A1 | 1/2013 | Hoekstra et al. |
| 2013/0338172 A1 | 12/2013 | Smyth et al. |
| 2014/0349973 A1 | 11/2014 | Hoekstra et al. |
| 2015/0051199 A1 | 2/2015 | Woodhead et al. |

FOREIGN PATENT DOCUMENTS

| | | |
|---|---|---|
| CN | 103857675 A | 6/2014 |
| CN | 103930418 A | 7/2014 |
| EP | 0 069 442 A1 | 1/1983 |
| JP | 58-032868 A | 2/1983 |
| WO | WO 2004/108684 A1 | 12/2004 |
| WO | WO 2011/133875 A2 | 10/2011 |
| WO | WO 2013/090210 A1 | 6/2013 |
| WO | WO 2014/201161 A1 | 12/2014 |
| WO | WO 2015/143142 A1 | 9/2015 |
| WO | WO 2016/149486 A1 | 9/2016 |

OTHER PUBLICATIONS

Chinese Office Action for Application No. 201280069217.7 dated Apr. 29, 2015.
Eurasian Office Action for Application No. 201491151/28 dated Mar. 12, 2015.
Extended European Search Report for Application No. 12858190.7 dated May 8, 2015.
Extended European Search Report for Application No. 18158614.0 dated May 4, 2018.
International Search Report and Written Opinion for Application No. PCT/US2012/068818 dated Mar. 19, 2013.
International Search Report and Written Opinion dated Nov. 18, 2016 in connection with Application No. PCT/US2016/052151.
International Search Report and Written Opinion dated Feb. 2, 2017 in connection with Application No. PCT/US2016/052300.
Invitation to Pay Additional Fees mailed Nov. 10, 2016 in connection with Application No. PCT/US2016/052300.
Böhme et al., Treatment of invasive fungal infections in cancer patients—recommendations of the Infectious Diseases Working Party (AGIHO) of the German Society of Hematology and Oncology (DGHO). Ann Hematol. Feb. 2009;88(2):97-110. doi: 10.1007/s00277-008-0622-5. Epub Oct. 14, 2008. Review.
Chen et al., Structural basis for multifunctional roles of mammalian aminopeptidase N. Proc Natl Acad Sci U S A. Oct. 30, 2012;109(44):17966-71. doi: 10.1073/pnas.1210123109. Epub Oct. 15, 2012.
Cornelison, Human papillomavirus genotype 16 vaccines for cervical cancer prophylaxis and treatment. Curr Opin Oncol. Sep. 2000;12(5):466-73. Review.
Curtis et al., Naturally occurring thiophens. V. Acetylenic thiophens from the basidiomycete Daedalea juniperina Murr. J Chem Soc Perkin 1. 1969;13:1813-8.
Eto et al., New antifungal 1,2,4-triazoles with difluoro(heteroaryl)methyl moiety. Chem Pharm Bull (Tokyo). Jul. 2000;48(7):982-90.
Swenson, New insights into carbonic anhydrase inhibition, vasodilation, and treatment of hypertensive-related diseases. Curr Hypertens Rep. Sep. 2014;16(9):467. doi: 10.1007/s11906-014-0467-3. Review.

*Primary Examiner* — Patricia L Morris
(74) *Attorney, Agent, or Firm* — Brinks Gilson & Lione

(57) ABSTRACT

The present invention relates to a process for preparing a compound of 5 or 5*, or a mixture thereof, and/or a compound of 14 or 14*, or a mixture thereof, that is useful as an antifungal agent. In particular, the invention seeks to provide new methodology for preparing compounds 7, 7* and 11, 11* and substituted derivatives thereof.

27 Claims, No Drawings

ANTIFUNGAL COMPOUND PROCESS

CROSS-REFERENCE TO RELATED APPLICATIONS

This application is the National Phase under 35 U.S.C. § 371 of PCT International Application No. PCT/US2016/052151, filed Sep. 16, 2016, which claims priority to U.S. Provisional Application No. 62/220,384, filed Sep. 18, 2015 and U.S. Provisional Application No. 62/275,504, filed Jan. 6, 2016, each of which is incorporated herein by reference in its entirety.

BACKGROUND

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as CYP2C9, CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof. Similarly, methods of synthesizing such therapeutic agents in the laboratory and, ultimately, commercial scale is needed. Addition of metal-based nucleophiles (Zn, Zr, Ce, Ti, Mg, Mn, Li) to azole-methyl substituted ketones have been effected in the synthesis of voriconazole (M. Butters, Org. Process Res. Dev. 2001, 5, 28-36). The nucleophile in these examples was an ethylpyrimidine substrate. Similarly, optically active azole-methyl epoxide has been prepared as precursor electrophile toward the synthesis of ravuconazole (A. Tsuruoka, Chem. Pharm. Bull. 1998, 46, 623-630). Despite this, the development of methodology with improved efficiency and selectivity is desirable.

BRIEF SUMMARY OF THE INVENTION

The invention is directed toward methods of synthesis of compound 5 or compound 5*. The methods can comprise the compounds herein. A first aspect of the invention relates to a process for preparing a compound of formula 5 or 5*, or a pharmaceutically acceptable salt, hydrate, solvate, complex or prodrug thereof.

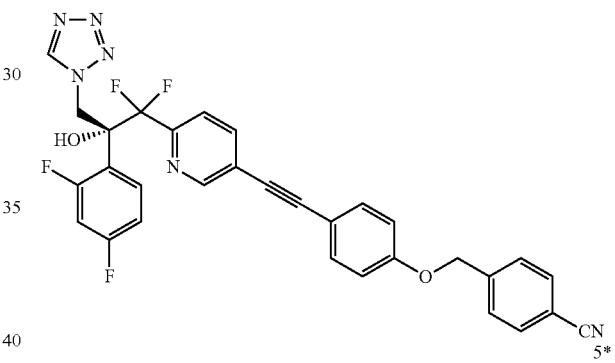

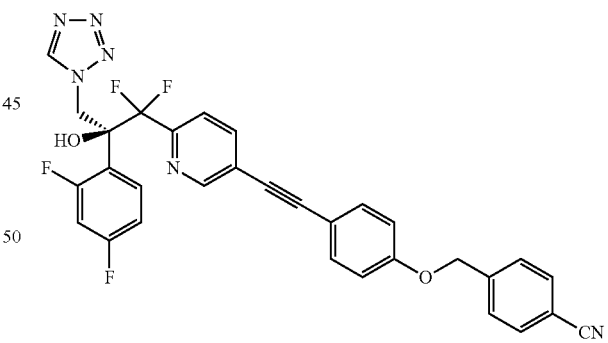

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967);

"Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In the following aspects, reference is made to the schemes and compounds herein, including the reagents and reaction conditions delineated herein. Other aspects include any of the compounds, reagents, transformations or methods thereof delineated in the examples herein (in whole or in part), including as embodiments with single elements (e.g., compounds or transformations) or embodiments including multiple elements (e.g., compounds or transformations).

In one aspect, the invention provides a process to prepare a compound of Formula 1 or 1*, or mixture thereof:

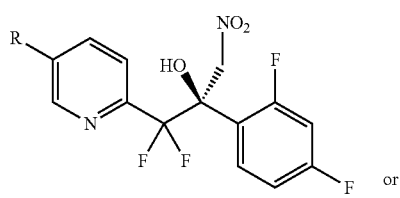

1

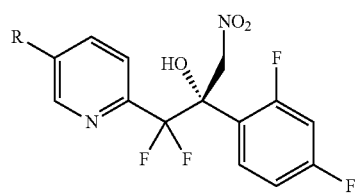

1* the process comprising reacting a compound of Formula 2:

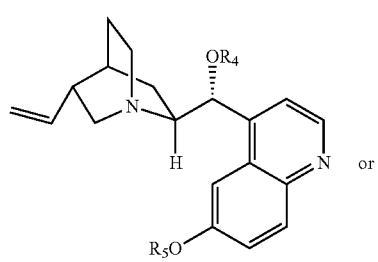

2 with nitromethane in the presence of a chiral catalyst of Formula 3 or 3*:

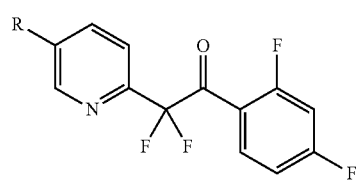

3 or

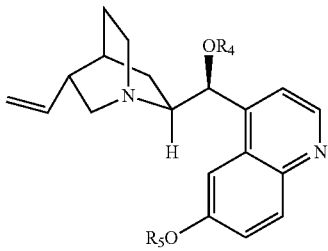

3* wherein each $R_4$ is independently H, optionally substituted alkyl, —(C=O)-optionally substituted alkyl, —(C=O)-optionally substituted aryl; and each $R_5$ is independently H, optionally substituted alkyl, optionally substituted arylalkyl, or optionally substituted aryl;

to provide a compound of Formula 1 or 1*, or mixture thereof;

wherein each R is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, —O(SO$_2$)-substituted aryl, ethynyl, substituted ethynyl, or

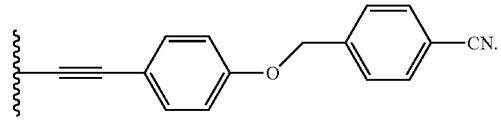 [SMILES: *C#Cc1ccc(OCc2ccc(C#N)cc2)cc1]

In another aspect, the invention provides a process to prepare a compound of Formula 1 or 1*, or mixture thereof:

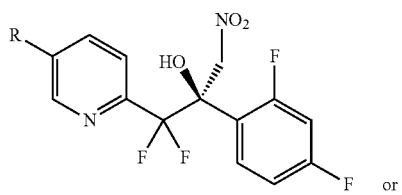

1 or

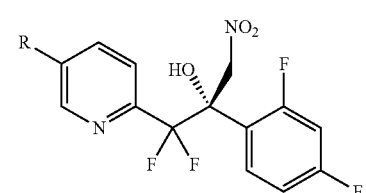

1* the process comprising reacting a compound of Formula 2:

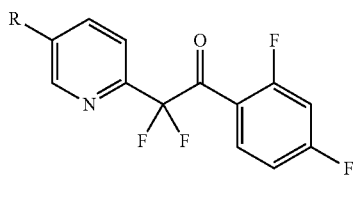

with nitromethane in the presence of a chiral catalyst of Formula 3:

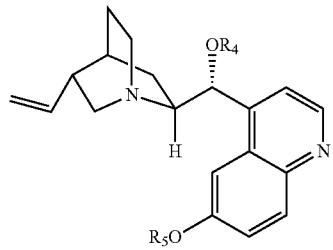

wherein R₄ is H, optionally substituted alkyl, —(C=O)-optionally substituted alkyl, —(C=O)-optionally substituted aryl; and R₅ is H, optionally substituted alkyl, optionally substituted arylalkyl, or optionally substituted aryl;

to provide a compound of Formula 1 or 1*, or mixture thereof;

wherein each R is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, —O(SO₂)-substituted aryl, ethynyl, substituted ethynyl, or

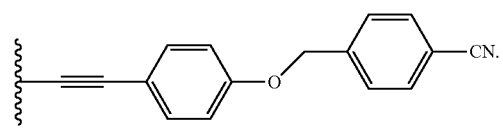 [SMILES: *C#Cc1ccc(OCc2ccc(C#N)cc2)cc1]

In another aspect, the chiral catalyst is

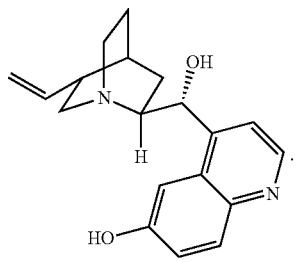 [SMILES: C=CC1CN2CCC1CC2[C@H](O)c1ccnc2ccc(O)cc12]

In another aspect, the mole percent of

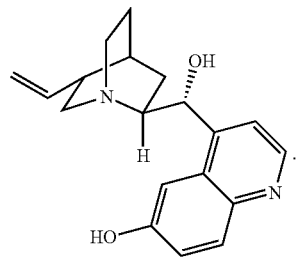 [SMILES: C=CC1CN2CCC1CC2[C@H](O)c1ccnc2ccc(O)cc12]

used in any of the processes presented herein is about 0.5-50.
In another aspect, the mole percent of

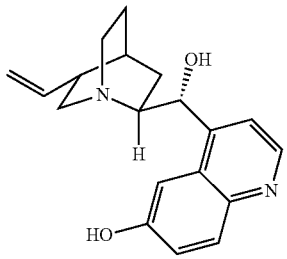 [SMILES: C=CC1CN2CCC1CC2[C@H](O)c1ccnc2ccc(O)cc12]

used in any of the processes presented herein is about 0.5-25.
In another aspect, the mole percent of

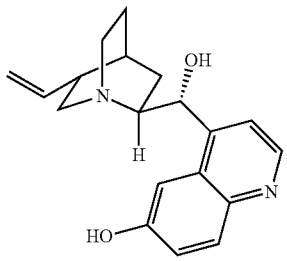 [SMILES: C=CC1CN2CCC1CC2[C@H](O)c1ccnc2ccc(O)cc12]

used in any of the processes presented herein is about 1-10.
In another aspect, the mole percent of

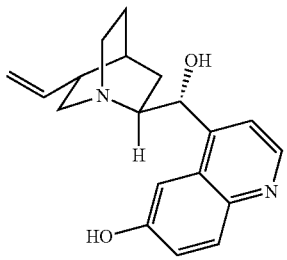 [SMILES: C=CC1CN2CCC1CC2[C@H](O)c1ccnc2ccc(O)cc12]

used in any of the processes presented herein is about 5.

In another embodiment, the number of equivalents of nitromethane used in any of the processes presented herein is about 1-25. In another aspect, the number of equivalents of nitromethane used in any of the processes presented herein is about 5-15. In another aspect, the number of equivalents of nitromethane used in any of the processes presented herein is about 10.

In another embodiment, the invention provides a process for reducing a compound of Formula 1 or 1*, or mixture thereof:

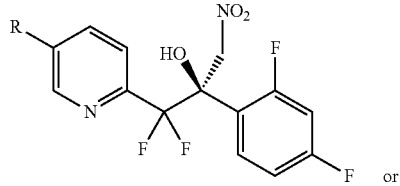

1 or

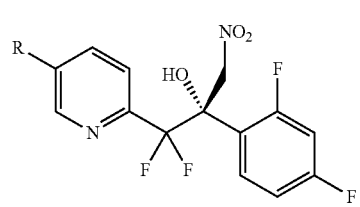

1* to afford a compound of Formula 4 or 4*, or mixture thereof:

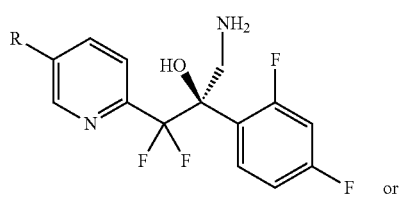

4 or

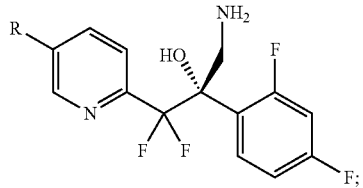

4*;

wherein each R is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, —O(SO₂)-substituted aryl, ethynyl, substituted ethynyl, or

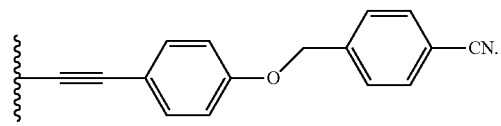 [SMILES: *C#Cc1ccc(OCc2ccc(C#N)cc2)cc1]

In another embodiment, the invention provides a process to prepare a compound of Formula 5 or 5*, or mixture thereof:

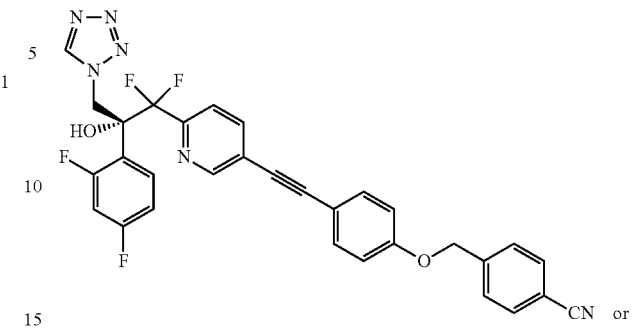

5 or

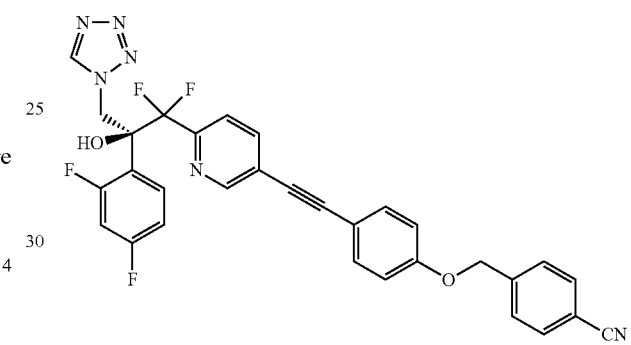

5* the method comprising:
a. reacting a compound of Formula 6:

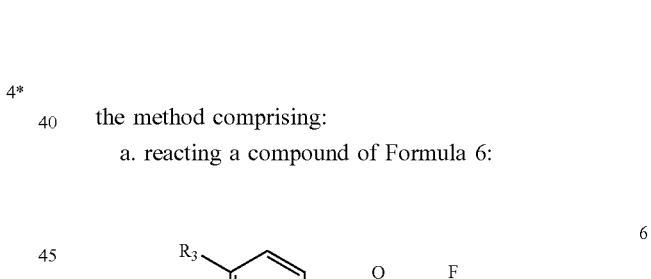

6 with nitromethane in the presence of a chiral catalyst of Formula 3 or 3*:

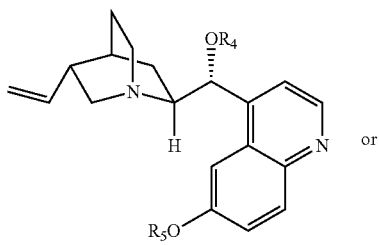

3 or

-continued

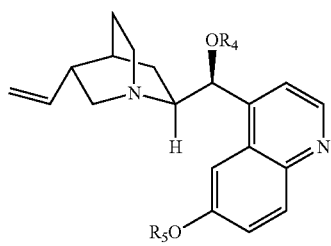

3* wherein each $R_4$ is independently H, optionally substituted alkyl, —(C═O)-optionally substituted alkyl, —(C═O)-optionally substituted aryl; and each $R_5$ is independently H, optionally substituted alkyl, optionally substituted arylalkyl, or optionally substituted aryl;

to provide a compound of Formula 7 or 7*, or mixture thereof; and

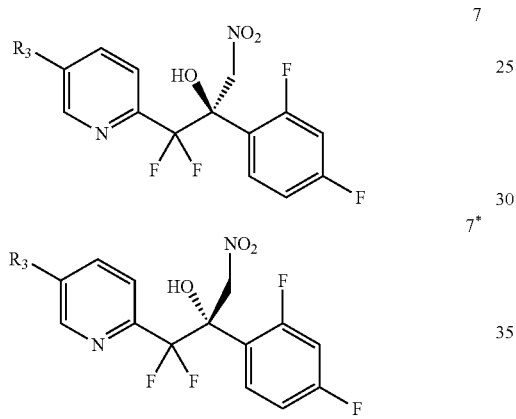

7

7* b. conversion of a compound of Formula 7 or 7*, or mixture thereof, to a compound of Formula 5 or 5*, or mixture thereof;

wherein each $R_3$ is independently halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O($SO_2$)-alkyl, —O($SO_2$)-substituted alkyl, —O($SO_2$)-aryl, or —O($SO_2$)-substituted aryl.

In another embodiment, the invention provides a process to prepare a compound of Formula 5 or 5*, or mixture thereof:

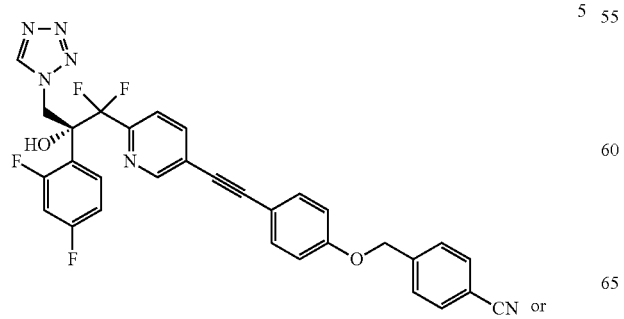

5

-continued

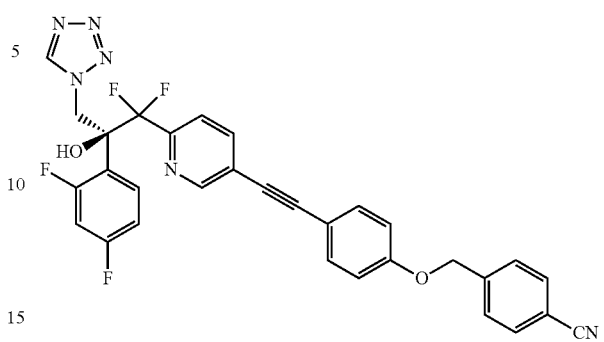

5* the method comprising:
a. reacting a compound of Formula 6:

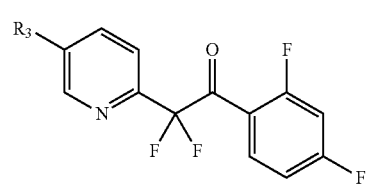

6 with nitromethane in the presence of a chiral catalyst of Formula 3:

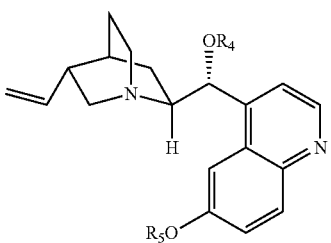

3 wherein $R_4$ is H, optionally substituted alkyl, —(C═O)-optionally substituted alkyl, —(C═O)-optionally substituted aryl; and $R_5$ is H, optionally substituted alkyl, optionally substituted arylalkyl, or optionally substituted aryl;

to provide a compound of Formula 7 or 7*, or mixture thereof; and

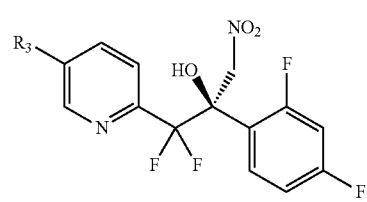

7

-continued

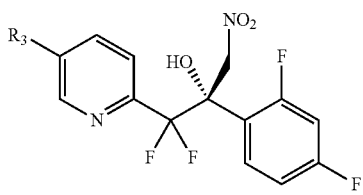
7* b. conversion of a compound of Formula 7 or 7*, or mixture thereof, to a compound of Formula 5 or 5*, or mixture thereof;

wherein each $R_3$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, any of the embodiments presented herein may comprise:
arylation of ester 9;

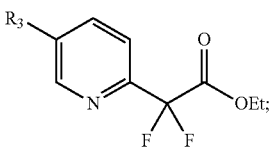
9 to afford ketone 6;

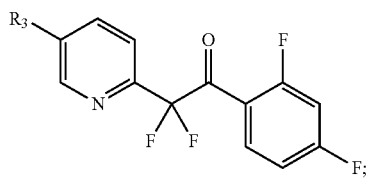
6 wherein each $R_3$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the method comprises reacting ester 9 with

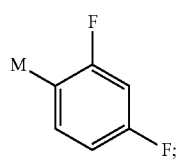

wherein M is Mg, MgX, Li, or AlX$_2$; X is halogen, alkyl, or aryl; and $R_3$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, M is Mg or MgX, and X is halogen.

In another aspect, any of the embodiments presented herein may comprise:
a. amidation of ester 9;

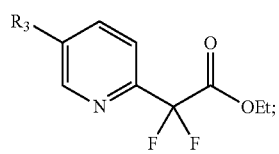
9 to afford morpholine amide 10; and

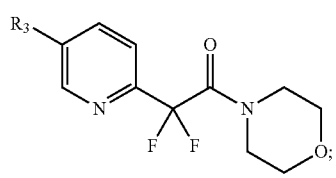
10 b. arylation of morpholine amide 10 to afford ketone 6;

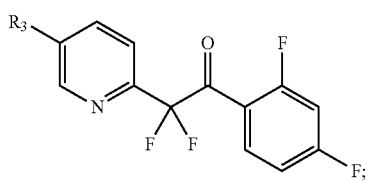
6 wherein each $R_3$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, step b. comprises reacting morpholine amide 10 with

wherein M is Mg, MgX, Li, or AlX$_2$; X is halogen, alkyl, or aryl; and each $R_3$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, M is Mg or MgX, and X is halogen.

In another aspect, any of the embodiments presented herein may comprise:

reducing a compound of Formula 7 or 7*, or mixture thereof:

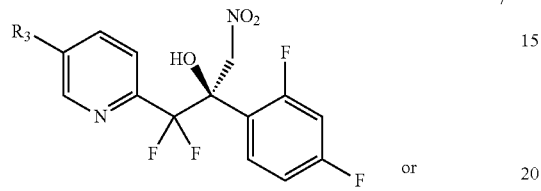

7 or

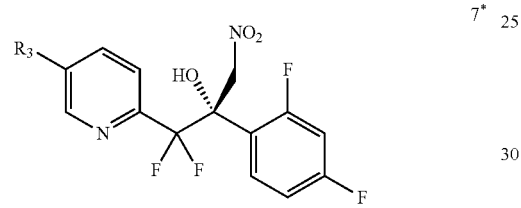

7* to afford a compound of Formula 11 or 11*, or mixture thereof:

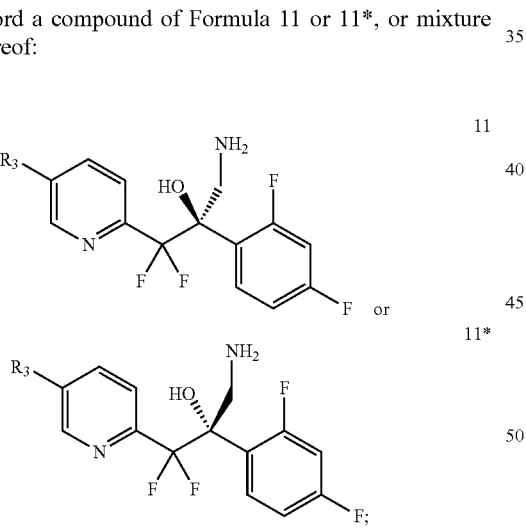

11 or

11* wherein each R$_3$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, any of the embodiments presented herein may comprise:

a. alkynylating a compound of Formula 11 or 11*, or mixture thereof,

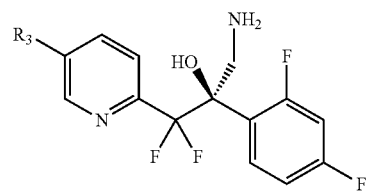

11

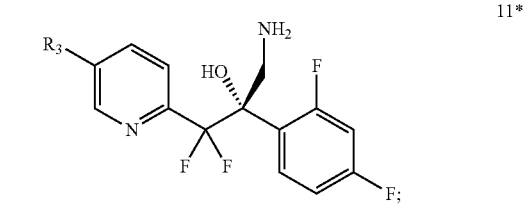

11* to afford a compound of Formula 12 or 12*, or mixture thereof; and

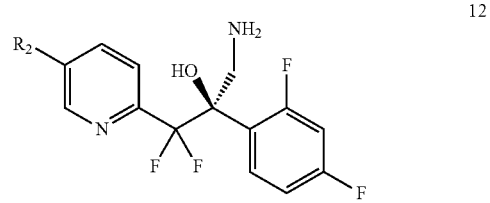

12

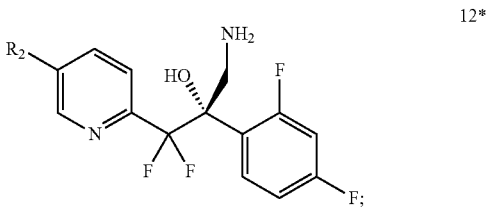

12* b. forming the tetrazole of a compound of Formula 12 or 12*, or mixture thereof, to afford a compound of Formula 18 or 18*, or mixture thereof;

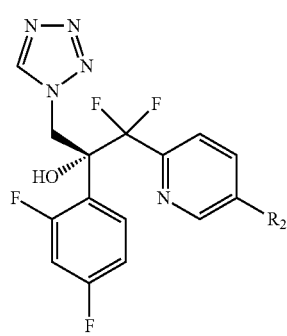

18

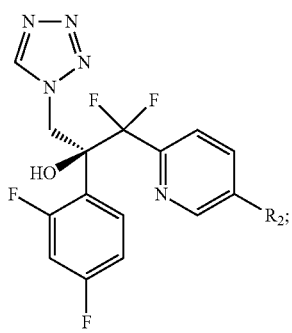

18* wherein each $R_2$ is independently ethynyl, substituted ethynyl, or

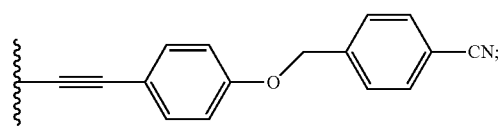

and each $R_3$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, any of the embodiments presented herein may comprise:

a. forming the tetrazole of a compound of Formula 11 or 11*, or mixture thereof,

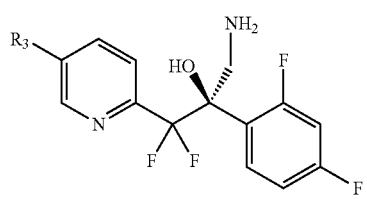

11

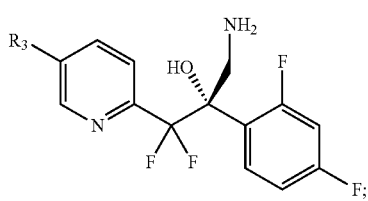

11* to afford a compound of Formula 13 or 13*, or mixture thereof; and

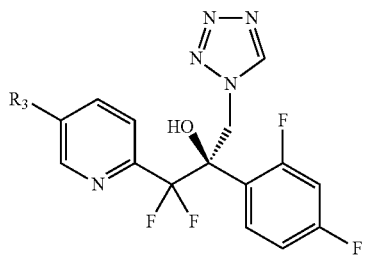

13

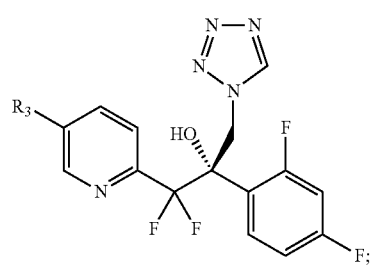

13* b. alkynylating a compound of Formula 13 or 13*, or mixture thereof, to afford a compound of Formula 18 or 18*, or mixture thereof;

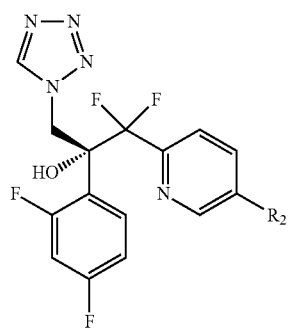

18

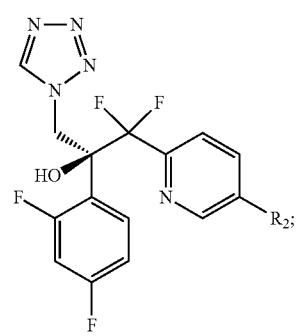

18* wherein each $R_2$ is independently ethynyl, substituted ethynyl, or

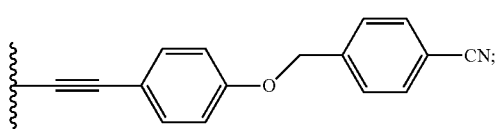 [SMILES: *C#Cc1ccc(OCc2ccc(C#N)cc2)cc1]

and each R₃ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In any of the above embodiments, when R₂ in any of Formula 18 or 18* is ethynyl, the processes may further comprise coupling the compound of Formula 18 or 18*, wherein R₂ is ethynyl, with

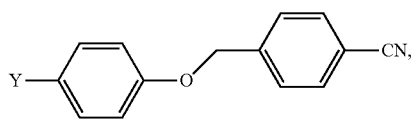

wherein Y is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl, to afford of compound of Formula 5 or 5*, or a mixture thereof:

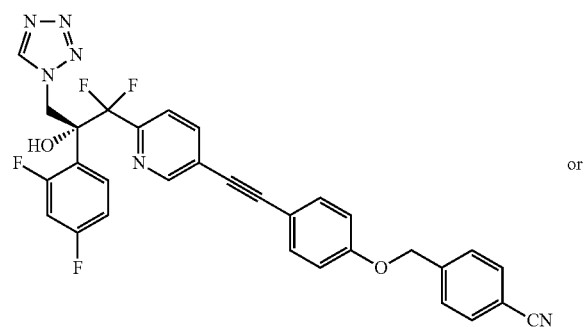

5 or

5*

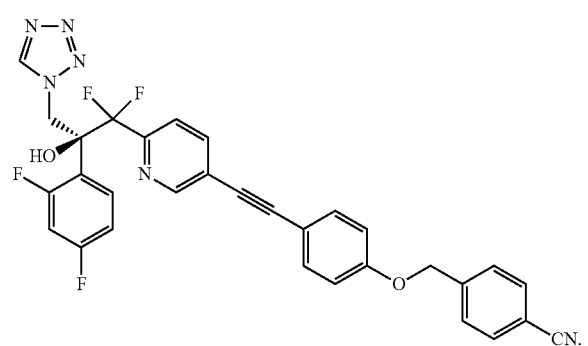

In any of the above embodiments, when R₂ in any of Formula 18 or 18* is ethynyl, the processes may further comprise:

a. coupling the compound of Formula 18 or 18*, wherein R₂ is ethynyl, with

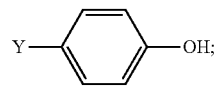

b. alkylating the product from step a. with

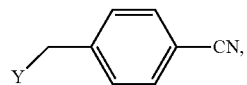

to afford of compound of Formula 5 or 5*, or a mixture thereof:

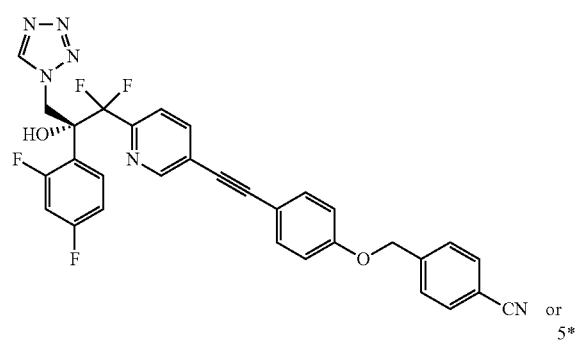

5 or

5*

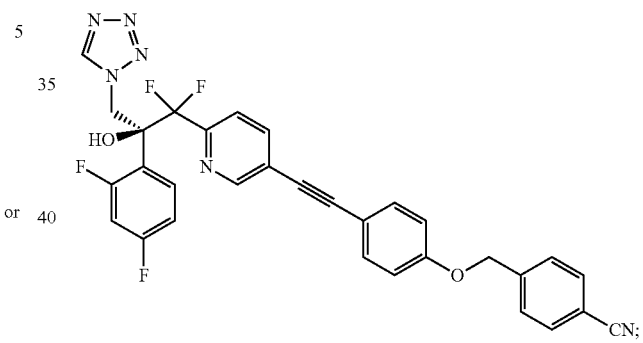

wherein each Y is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In the asymmetric Henry reaction process step, in one aspect the reaction is performed (and catalyst selected) such that the enantiomeric ratio of products is greater than 50:50; greater than 60:40; greater than 72:25; greater than 80:20; greater than 85:15; greater than 90:10; greater than 95:5; or greater than 97:3.

In the aforementioned processes, "alkynylkating" or "alkynylation" can be accomplished by any suitable coupling reaction process (e.g., Sonogashira coupling, Grignard reaction, Heck coupling, Negishi coupling, Suzuki coupling, Suzuki-Miyaura reaction, Kumada cross-coupling, Castro-Stephens coupling, Ullmann reaction, Weinreb ketone synthesis, Stille coupling, Stille-Kelly coupling, and the like), including organometallic coupling reactions known in the art, including use of organoborane, organoboronate, organocopper, organopalladium, organonickel, organosilicon, organolead, organomagnesium, organoiron, organolithium, and/or organotin reagents and methods known in the art.

In another aspect, the invention provides a process to prepare compound 5 or 5*, or a mixture thereof:

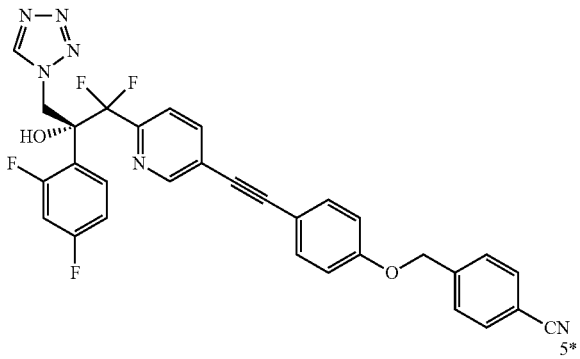

5

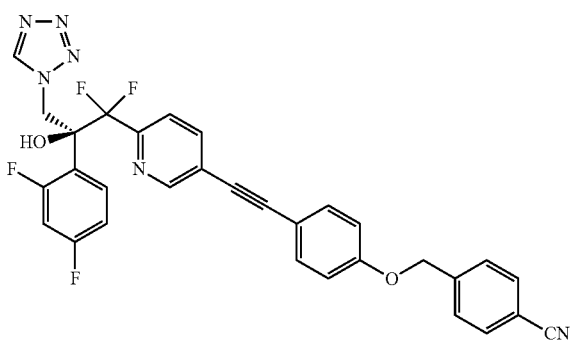

5* comprising converting amide 15c:

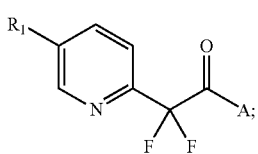

15c to compound 5 or 5*, or mixtures thereof;
wherein R₁ is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl;
A is N(OMe)Me, NR₈R₉, or

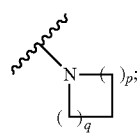

p is 1, 2, 3, or 4;
q is 1, 2, 3, or 4;
each R₈ and R₉ is independently H, alkyl, substituted alkyl, aryl, substituted aryl, heteroaryl, or substituted heteroaryl.

In another aspect, the invention provides a process to prepare compound 5 or 5*, or a mixture thereof:

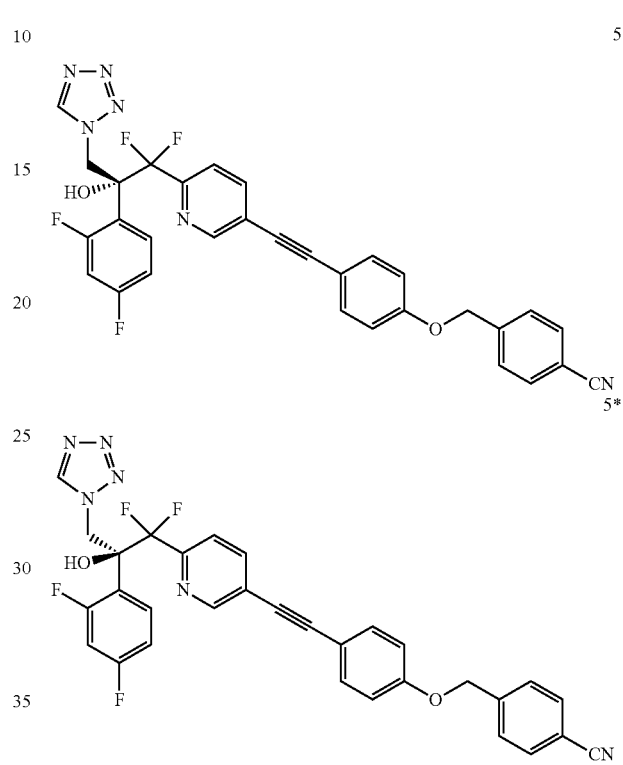

comprising converting amide 15c:

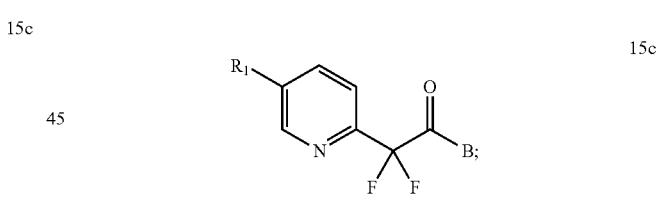

to compound 5 or 5*, or mixtures thereof;
wherein R₁ is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl;
B is N(OMe)Me, NR₈R₉, or

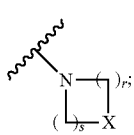

X is O, NR$_8$, or S;

r is 2, 3, or 4;

s is 2, 3, or 4;

each R$_8$ and R$_9$ is independently H, alkyl, substituted alkyl, aryl, substituted aryl, heteroaryl, or substituted heteroaryl.

In another aspect, the invention provides a process to prepare compound 5 or 5*, or a mixture thereof:

5

[Structure of compound 5: tetrazole-CH$_2$-C(OH)(2,4-difluorophenyl)-CF$_2$-pyridine-C≡C-phenyl-O-CH$_2$-phenyl-CN]

5*

[Structure of compound 5*: stereoisomer with wedge bond]

comprising converting morpholine amide 15b:

15b

[Structure of 15b: R$_1$-pyridine-CF$_2$-C(=O)-morpholine]

to compound 5 or 5*, or a mixture thereof;
wherein R$_1$ is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process comprising reacting morpholine amide 15b:

15b

[Structure of 15b]

with

[Structure: M-2,4-difluorophenyl]

wherein M is Mg or MgX; and X is halogen;
to provide a compound of 5 or 5*, or a mixture thereof:

5

[Structure of compound 5]

5*

[Structure of compound 5*]

wherein R$_1$ is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process comprising reacting morpholine amide 15b:

[Structure 15b: pyridine with R₁, connected to C(F)(F)-C(=O)-morpholine]

with

[Structure: 2,4-difluorophenyl-M]

wherein M is Mg, MgX, Li, or AlX₂; and X is halogen, alkyl, or aryl;

to provide compound 5 or 5*, or a mixture thereof:

[Structure 5: tetrazole-CH₂-C(OH)(2,4-difluorophenyl)-C(F)(F)-pyridine-C≡C-phenyl-O-CH₂-phenyl-CN]

[Structure 5*: stereoisomer of 5]

wherein R₁ is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, any of the embodiments presented herein may comprise amidation of ester 15:

[Structure 15: R₁-pyridine-C(F)(F)-C(=O)-OEt]

to provide morpholine amide 15b:

[Structure 15b: R₁-pyridine-C(F)(F)-C(=O)-morpholine]

wherein each R₁ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, any of the embodiments presented herein may comprise amidation of ester 15d:

[Structure 15d: R₁-pyridine-C(F)(F)-C(=O)-O-R₈]

to provide morpholine amide 15b:

[Structure 15b: R₁-pyridine-C(F)(F)-C(=O)-morpholine]

wherein each R₁ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl; and $R_8$ is H, alkyl, substituted alkyl, aryl, substituted aryl, heteroaryl, or substituted heteroaryl.

In another aspect, any of the embodiments presented herein may comprise reacting ester 15:

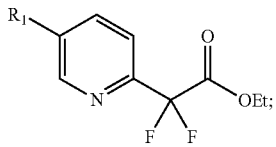

with morpholine to provide morpholine amide 15b:

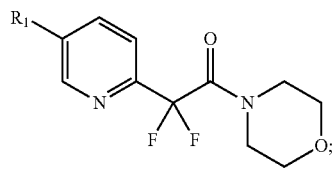

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, any of the embodiments presented herein may comprise a process of enriching the enantiomeric purity of an enantiomeric compound mixture (e.g., Compounds 7/7*, or a mixture thereof and/or 4/4*, or a mixture thereof and/or 11/11*, or a mixture thereof, and/or 12/12*, or a mixture thereof and/or 18/18*, or a mixture thereof), comprising:
(i) crystallizing said enantiomeric compound mixture with a chiral acid in a suitable solvent or solvent mixture, wherein:

the suitable solvent or solvent mixture is selected from acetonitrile, isopropanol, ethanol, water, methanol, or combinations thereof;
(ii) isolating the enantio-enriched compound mixture; and
(iii) free-basing the enantio-enriched chiral salt mixture to provide the enantio-enriched compound mixture.

In another aspect, the process of enriching the enantiomeric purity of an enantiomeric compound mixture further comprises reslurrying the enantio-enriched chiral salt mixture in a slurrying solvent or slurrying solvent mixture.

In another aspect, the chiral acid from any embodiment presented herein is selected from the group consisting of tartaric acid, di-benzoyltartaric acid, malic acid, camphoric acid, camphorsulfonic acid, ascorbic acid, and di-p-toluoyltartaric acid;

In another aspect, the suitable solvent or solvent mixture from any embodiments presented herein is 1-propanol, 1-butanol, ethyl acetate, tetrahydrofuran, 2-methyltetrahydrofuran, toluene, methyl tert-butylether, diethyl ether, dichloromethane, 1,4-dioxane, 1,2-dimethoxyethane, isopropyl acetate, heptane, hexane, cyclohexane, or octane, or combinations thereof.

In another aspect, the slurrying solvent solvent or slurrying solvent mixture from any embodiments presented herein is 1-propanol, 1-butanol, ethyl acetate, tetrahydrofuran, 2-methyltetrahydrofuran, toluene, methyl tert-butylether, diethyl ether, dichloromethane, 1,4-dioxane, 1,2-dimethoxyethane, isopropyl acetate, heptane, hexane, cyclohexane, or octane, or combinations thereof.

In another aspect, the suitable solvent or solvent mixture from any embodiments presented herein is a) acetonitrile or b) a mixture of acetonitrile and isopropanol. Alternatively, another aspect is where the mixture of acetonitrile and isopropanol comprises 80-90% acetonitrile and 10-20% isopropanol.

In another aspect, the slurrying solvent or slurrying solvent mixture from any embodiments presented herein is a) acetonitrile or b) a mixture of acetonitrile and isopropanol. Alternatively, another aspect is where the mixture of acetonitrile and isopropanol comprises 80-90% acetonitrile and 10-20% isopropanol.

In another aspect, any of the embodiments presented herein further comprises a process to prepare a compound of formula 14 or 14*, or a mixture thereof, comprising:

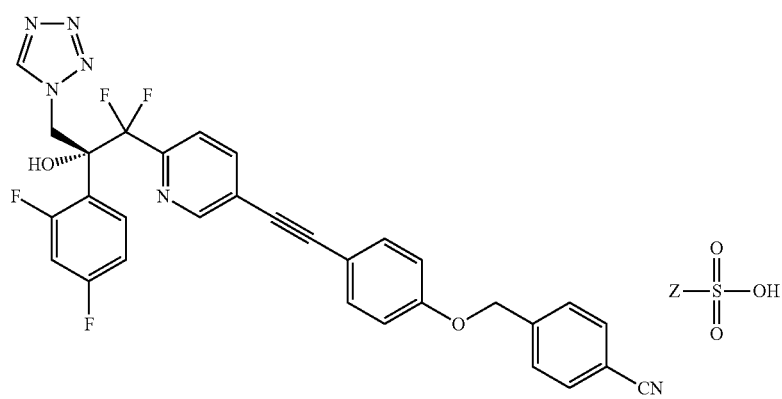

or

-continued

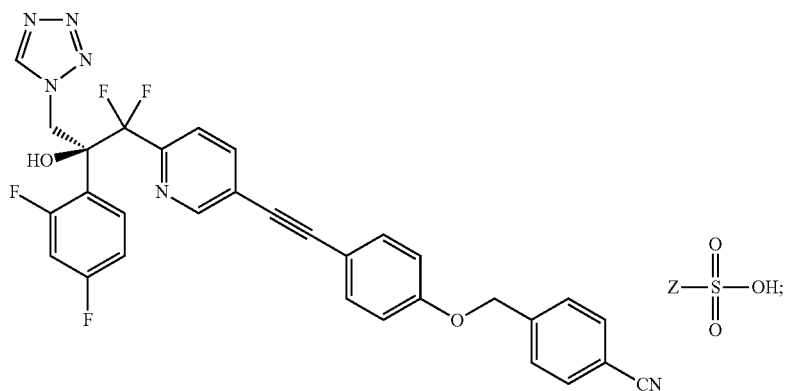

(i) combining compound 5 or 5*, or a mixture thereof, a sulfonic acid

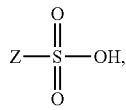

and a crystallization solvent or crystallization solvent mixture;

5

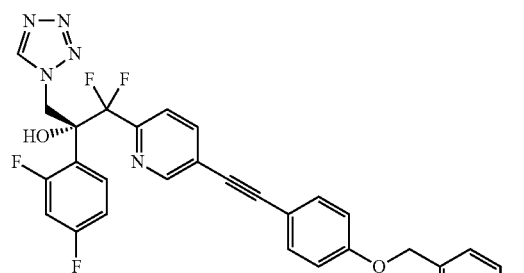

or 5*

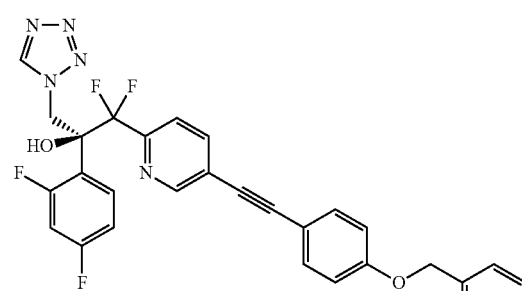

(ii) diluting the mixture from step (i) with a crystallization co-solvent or crystallization co-solvent mixture; and
(iii) isolating a compound of formula 14 or 14*, or a mixture thereof;
wherein each Z is independently aryl, substituted aryl, alkyl, or substituted alkyl.

In another aspect, Z from any of the embodiments presented herein is phenyl, p-tolyl, methyl, or ethyl. In certain embodiments, Z is p-tolyl.

In certain embodiments, the compound of Formula 14 or 14* is

14

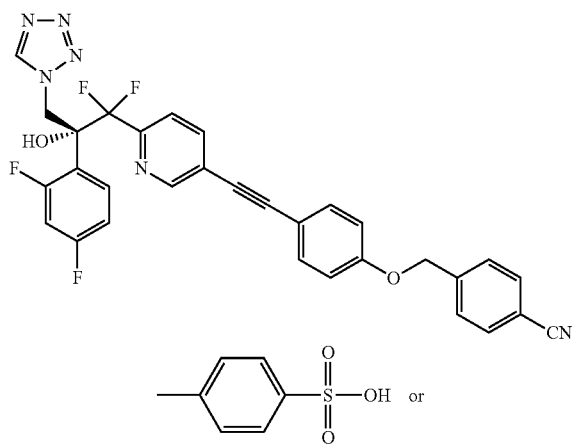

14*

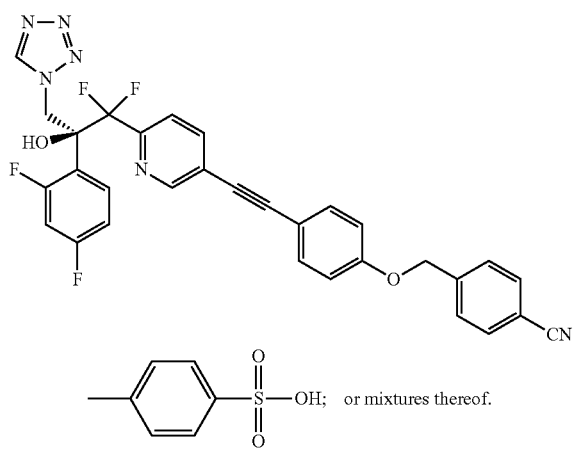

In another aspect, the crystallization solvent or crystallization solvent mixture from any of the embodiments presented herein is ethyl acetate, isopropyl acetate, ethanol, methanol, or acetonitrile, or combinations thereof.

In another aspect, the crystallization co-solvent or crystallization co-solvent mixture from any of the embodiments presented herein is pentane, methyl t-butylether, hexane, heptane, or toluene, or combinations thereof.

In another aspect, any of the embodiments presented herein may comprise repeating the enantio-enrichment step(s) until desired level of enantio-enrichment is attained.

In other aspects, the invention provides a compound of any of the formulae herein, wherein the compound inhibits (or is identified to inhibit) lanosterol demethylase (CYP51).

In another aspect, the invention provides a pharmaceutical composition comprising a compound of any formulae herein and a pharmaceutically acceptable carrier.

In other aspects, the invention provides a method of modulating metalloenzyme activity in a subject, comprising contacting the subject with a compound of any formulae herein, in an amount and under conditions sufficient to modulate metalloenzyme activity.

In one aspect, the invention provides a method of treating a subject suffering from or susceptible to a metalloenzyme-related disorder or disease, comprising administering to the subject an effective amount of a compound or pharmaceutical composition of any formulae herein.

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of any formulae herein, such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any formulae herein, such that metalloenzyme activity in said subject is modulated (e.g., down regulated, inhibited). In another aspect, the compounds delineated herein preferentially target cancer cells over nontransformed cells.

DETAILED DESCRIPTION

Definitions

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate".

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a", "an", and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise", "comprises", and "comprising" are used in a non-exclusive sense, except where the context requires otherwise.

As used herein, the term "about", when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore, the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "haloalkoxy" refers to an —O-alkyl radical that is substituted by one or more halo substituents. Examples of haloalkoxy groups include trifluoromethoxy and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiiranyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me) C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database. The invention includes the intermediate compounds used in making the compounds of the formulae herein as well as methods of making such compounds and intermediates, including without limitation those as specifically described in the examples herein.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Pharmaceutical Compositions

In one aspect, the invention provides a pharmaceutical composition comprising a compound of any formulae herein and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In one aspect, the invention provides a kit comprising an effective amount of a compound of any formulae herein, in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, ophthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro-ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH 5 to pH 7, with a pH of about pH 5.5 being typical.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound (s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Agricultural Applications

The compounds and compositions herein can be used in methods of modulating metalloenzyme activity in a microorganism on a plant comprising contacting a compound (or composition) herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of 5 or 5*

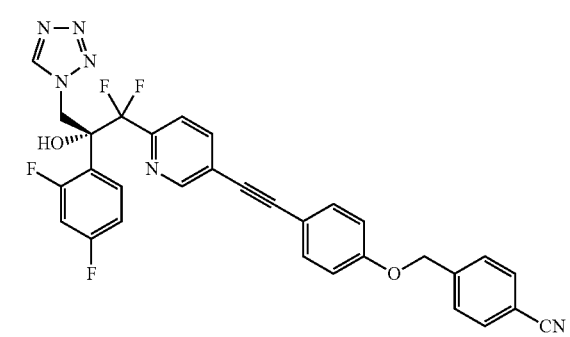

-continued

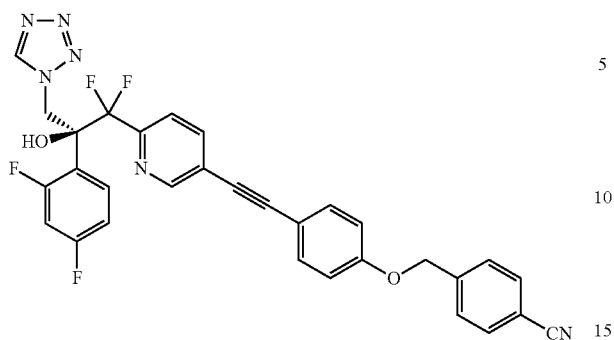

5*

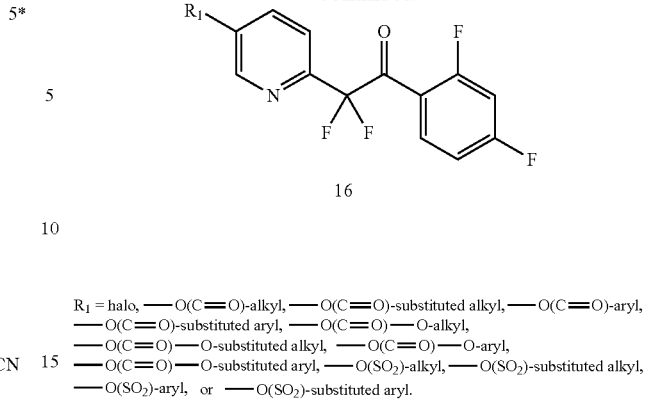

16

$R_1$ = halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

A process to prepare enantiopure compound 5 or 5* is disclosed. Syntheses of 5 or 5* may be accomplished using the example syntheses that are shown below (Schemes 1-4). The preparation of precursor ketone 16-Br is performed starting with reaction of 2,5-dibromopyridine with ethyl 2-bromo-difluoroacetate to produce ester 15-Br. This ester can be reacted with morpholine to furnish morpholine amide 15b-Br, followed by arylation to provide ketone 16-Br. Alternatively, ketone 16-Br can be afforded directly from ester 15-Br, as shown in Scheme 1.

Ketone 16 may be used to prepare 13 (or 13*, the enantiomer of 13, or mixtures thereof) or 5 (or 5*, the enantiomer of 5, or mixtures thereof) by the following three-step process (Scheme 3). In the presence of a chiral catalyst/reagent (e.g., compounds of Formula 3 or 3*), Scheme 1. Synthesis of ketone 16-Br

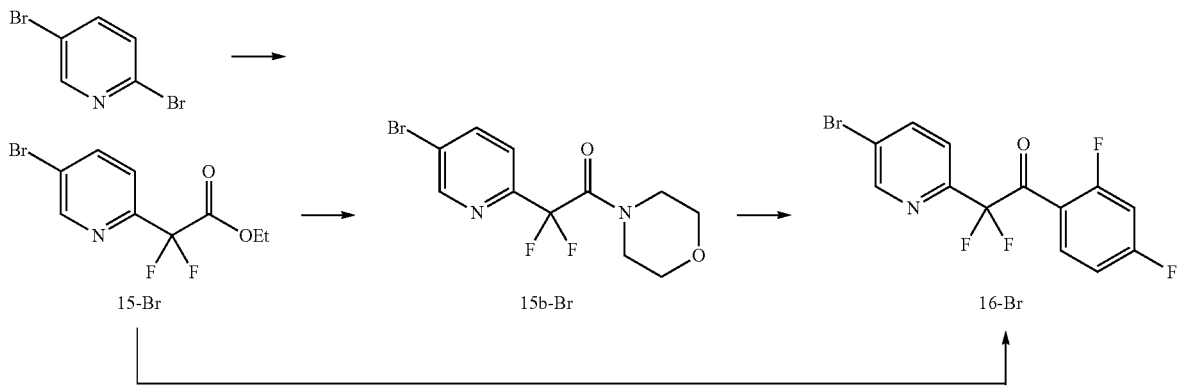

Ketone 16 may be prepared in an analogous fashion as described in Scheme 1 starting from corresponding substituted 2-bromo-pyridines, which can be prepared according to synthetic transformations known in the art and contained in the references cited herein (Scheme 2).

Scheme 2. Synthesis of ketone 16

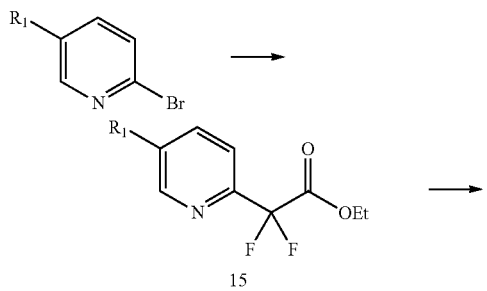

base-treated nitromethane is added to 16 or 16-1 to furnish 7 (or 7*, the enantiomer of 7, or mixtures thereof) or 7-1 (or 7*-1, the enantiomer of 7-1, or mixtures thereof), respectively. Reduction of 7 (or 7*, the enantiomer of 7, or mixtures thereof) or 7-1 (or 7*-1, the enantiomer of 7-1, or mixtures thereof) (e.g., hydrogenation) produces 11 (or 11*, the enantiomer of 11, or mixtures thereof) or 4 (or 4*, the enantiomer of 4, or mixtures thereof). Annulation of 11 (or 11*, the enantiomer of 11, or mixtures thereof) or 4 (or 4*, the enantiomer of 4, or mixtures thereof) by treatment with sodium azide/trimethylorthoformate furnishes tetrazoles 13 (or 13*, the enantiomer of 13, or mixtures thereof) or 5 (or 5*, the enantiomer of 5, or mixtures thereof). Sonogashira coupling of 13 or 13* (e.g., 13 or 13*, wherein R=Br; also referred to as 13-Br or 13*-Br) with 4-((4-ethynylphenoxy)methyl)benzonitrile produces 5 (or 5*, the enantiomer of 5, or mixtures thereof).

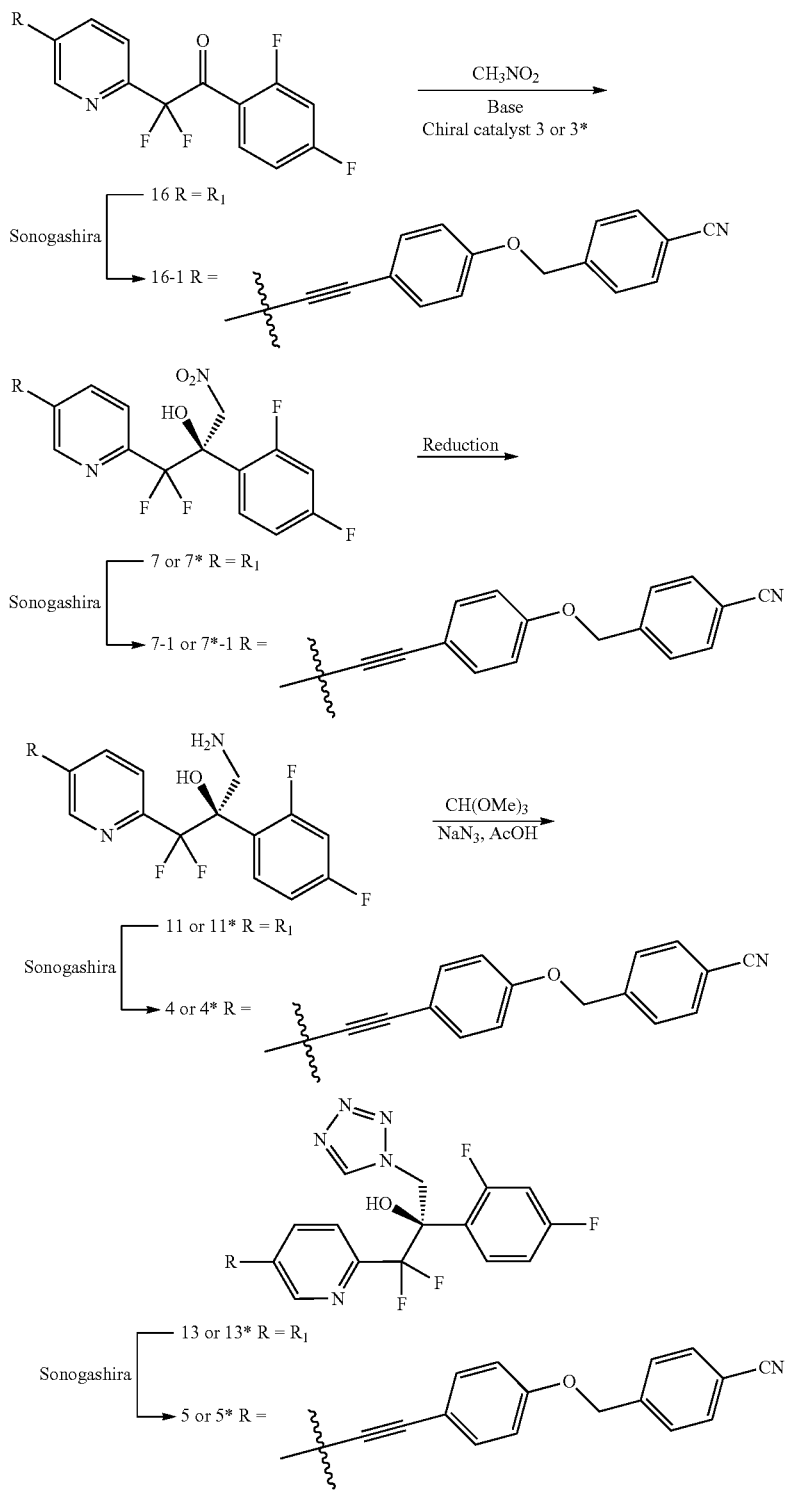
Scheme 3. Asymmetric Henry reaction
$R_1$ = halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

Compound 5 (or 5*, the enantiomer of 5, or mixtures thereof) prepared by any of the methods presented herein can be converted to a sulfonic acid salt of formula 14 (or 14*, the enantiomer of 14, or mixtures thereof), as shown in Scheme 4. This can be accomplished by a) combining compound 5 (or 5*, the enantiomer of 5, or mixtures thereof), a crystallization solvent or crystallization solvent mixture (e.g., EtOAc, iPrOAc, EtOH, MeOH, or acetonitrile, or combinations thereof), and a sulfonic acid

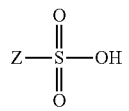

(e.g., Z=Ph, p-tolyl, Me, or Et), b) diluting the mixture with an appropriate crystallization co-solvent or crystallization co-solvent mixture (e.g., pentane, methyl t-butylether, hexane, heptane, or toluene, or combinations thereof), and c) filtering the mixture to obtain a sulfonic acid salt of formula 14 (or 14*, the enantiomer of 14, or mixtures thereof).

Scheme 4. Synthesis of a Sulfonic Acid Salt of Compound 5 or 5*

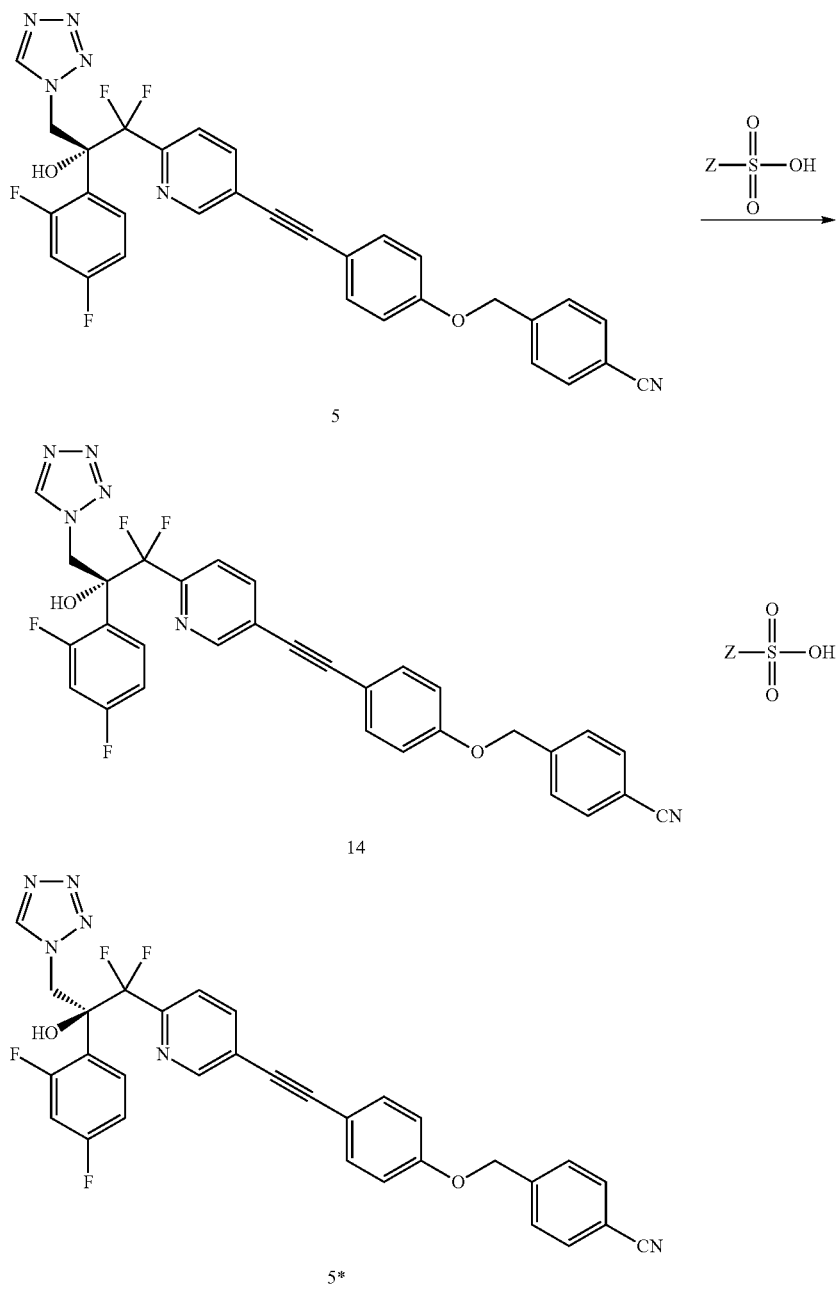

Abbreviations

| | |
|---|---|
| A % | area percent |
| AcOH | acetic acid |
| ACN | acetonitrile |
| Amt | amount |
| API | active pharmaceutical ingredient |
| Aq. | aqueous |
| Besylate, Bs | benzenesulfonic acid |
| DEA | diethylamine |
| DMF | N,N-dimethylformamide |
| DMSO | dimethylsulfoxide |
| Eq, equiv | equivalent |
| $Et_3N$ | triethylamine |
| EtOH | ethanol |
| FID | Flame ionization detector |
| GC | gas chromatography |
| HPLC | high performance liquid chromatography |
| ID | identification |
| IPA | isopropanol |
| iPrMgCl | isopropylmagnesium chloride |
| K-OtBu | potassium tert-butoxide |
| L-DTTA | di-O-p-toluoyl-L-tartaric acid |
| M | mole/liter |
| MeOH | methanol |
| Min | minutes |
| Mol | moles |
| MTBE | tert-butyl methyl ether |
| MW | molecular weight |
| NA | not applicable |
| $Na_2EDTA$-$2H_2O$ | ethylenediaminetetraacetic acid disodium salt dihydrate |
| ND | not detected |
| NMR | nuclear magnetic resonance spectroscopy |
| ppm | parts per million |
| THF | tetrahydrofuran |
| TLC | thin layer chromatography |
| TMS | trimethylsilyl |
| TMSI | trimethylsulfoxonium iodide |
| Tosylate, Ts | p-Toluenesulfonate |
| Wt | weight |
| XRD | x-ray powder diffraction |

The Following Analytical Techniques were Employed:

NMR:

NMR spectra were acquired on a Bruker Avance III FT-NMR instrument running at 400 MHz for $^1$H NMR. Spectra were referenced to TMS at 0.00 ppm.

In-Process GC Analyses:

Column: DB-624, 30 m×0.25 mm, 1.4 μm
Carrier gas: Hydrogen
Flow rate: 20 psi
Inlet Pressure: 20 psi
Split ratio: 50:1
Injection temperature: 250° C.
Inj volume: 1 μL
Oven program: 60° C. (3 min hold), 40° C./min to 240° C., 23 min hold at 240° C.
Detector: FID, 280° C.

In-Process HPLC Analyses:

Column: XBridge BEH C18, 2.1×50 mm, 2.5 μm
Mobile Phase: A=0.1% TFA/$H_2O$, B=0.1% TFA/ACN
Autosampler flush: 1:1 ACN/$H_2O$
Flow Rate: 0.8 ml/min
Temperature: 50° C.
Detector: UV 218 nm
Pump Parameters:

| Step | Segment Time | A | B | Curve |
|---|---|---|---|---|
| 0 | 0.5 | 90.0 | 10.0 | 0 |
| 1 | 0.5 | 90.0 | 10.0 | 0 |
| 2 | 6.0 | 10.0 | 90.0 | 1 |
| 3 | 1.1 | 10.0 | 90.0 | 0 |
| 4 | 4.0 | 90.0 | 10.0 | 0 |

HPLC Method Used in Assessing HPLC Purity of 5 and 5*; and 14 and 14*:

Column: Waters Sunfire C18, 3.5 m, 4.6×150 mm
Mobile Phase: A=0.05% $H_3PO_4$ in water, B=0.05% $H_3PO_4$ in ACN; C=NA; D=0.05% $H_3PO_4$ in methanol
Diluent: ACN
Autosampler flush: 1:1 ACN/H2O
Flow Rate: 1.0 ml/min
Temperature: 30° C.
Detector: UV 225 nm (reference=380 nm)
Pump Parameters:

| Step | Segment Time | A | B | D | Curve |
|---|---|---|---|---|---|
| 0 | 0.5 | 80.0 | 10.0 | 10.0 | 0 |
| 1 | 3.0 | 80.0 | 10.0 | 10.0 | 0 |
| 2 | 20.0 | 0.0 | 80.0 | 20.0 | 1 |
| 3 | 5.0 | 0.0 | 80.0 | 20.0 | 0 |
| 4 | 7.0 | 80.0 | 10.0 | 10.0 | 0 |

Process Development—Catalyst Selection

Table 1 captures the experimental conditions, % conversion, and enantiomeric ratio of the asymmetric Henry reaction for conversion of 16-Br to 1-Br and 1*-Br using various chiral catalyst systems.

TABLE 1

| Entry | ligand | Cu(II) | CH$_3$NO$_2$ | base | solvent | Temp/time | % Conv. | e.r. 1-Br: 1*-Br |
|---|---|---|---|---|---|---|---|---|
| 1 | — | — | 5 eq | K$_2$CO$_3$ (1.0 eq) | — | RT, 2 h | 92% | 50:50 |
| 2 | — | — | 10 eq | Et$_3$N (0.09 eq) | EtOH | RT, 45 h | — | 50:50 |
| 3 | 17 (0.05 eq) | — | 10 eq | — | THF | RT, 23.5 h | >95% | 90:10 |
| 4 | L2 (0.1 eq) | Cu(OTf)$_2$ (0.1 eq) | 10 eq | Et$_3$N (0.09 eq) | EtOH | RT, 70 h | 11.8% | 52:48 |
| 5 | L3 (0.1 eq) | Cu(OTf)$_2$ (0.1 eq) | 10 eq | Et$_3$N (0.09 eq) | EtOH | RT, 70 h | <1% | 50:50 |
| 6 | L4 (0.1 eq) | Cu(OTf)$_2$ (0.1 eq) | 10 eq | Et$_3$N (0.09 eq) | EtOH | RT, 16 h | 24% | 52:48 |
| 7 | L5 (0.1 eq) | Cu(OTf)$_2$ (0.1 eq) | 10 eq | Et$_3$N (0.09 eq) | EtOH | RT, 70 h | 11.6% | 50:50 |
| 8 | L7 (0.1 eq) | Cu(OTf)$_2$ (0.1 eq) | 10 eq | Et$_3$N (0.09 eq) | EtOH | RT, 16 h | No conv. | — |
| 9 | L10 (0.1 eq) | Cu(OTf)$_2$ (0.1 eq) | 10 eq | Et$_3$N (0.09 eq) | EtOH | RT, 16 h | No conv. | — |
| 10 | — | — | 10 eq | Et$_3$N (0.09 eq) | THF | RT, 18 h | 10.2% | 50:50 |
| 11 | — | Cu(OTf)$_2$ (0.1 eq) | 10 eq | Et$_3$N (0.09 eq) | THF | RT, 18 h | No conv. | 50:50 |
| 12 | L2 (0.1 eq) | Cu(OTf)$_2$ (0.1 eq) | 10 eq | Et$_3$N (0.09 eq) | THF | RT, 24 h | 4.7% | 51:49 |
| 13 | L3 (0.1 eq) | Cu(OTf)$_2$ (0.1 eq) | 10 eq | Et$_3$N (0.09 eq) | THF | RT, 24 h | 3.4% | 50:50 |
| 14 | L4 (0.1 eq) | Cu(OTf)$_2$ (0.1 eq) | 10 eq | Et$_3$N (0.09 eq) | THF | RT, 24 h | 48.7% | 50:50 |
| 15 | L5 (0.1 eq) | Cu(OTf)$_2$ (0.1 eq) | 10 eq | Et$_3$N (0.09 eq) | THF | RT, 24 h | 11.6% | 50:50 |

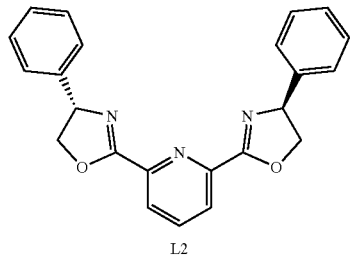 [SMILES: c1ccc([C@H]2COC(c3cccc(C4=N[C@@H](c5ccccc5)CO4)n3)=N2)cc1]

L2

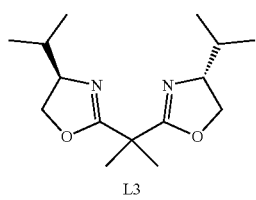 [SMILES: CC(C)[C@@H]1COC(C(C)(C)C2=N[C@H](C(C)C)CO2)=N1]

L3

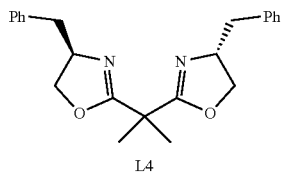 [SMILES: CC(C)(C1=N[C@H](Cc2ccccc2)CO1)C1=N[C@H](Cc2ccccc2)CO1]

L4

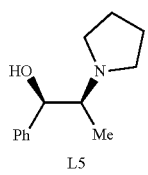 [SMILES: C[C@@H]([C@H](O)c1ccccc1)N1CCCC1]

L5

TABLE 1-continued

| Entry | ligand | Cu(II) | CH₃NO₂ | base | solvent | Temp/time | % Conv. | e.r. 1-Br: 1*-Br |
|---|---|---|---|---|---|---|---|---|

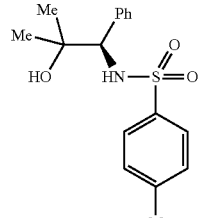

Asymmetric Henry reactions employing chiral ligands L2, L3, L4, L5, L7, and L10 resulted in low conversion to product and did not proceed in a stereoselective manner. However, the asymmetric Henry reaction using chiral ligand 17 provided complete conversion to product in a highly enantioselective fashion (see, Entry 3 from Table 1). Without being bound by any scientific theory, it is believed that the bicyclic structure and higher basicity of chiral ligands of Formula 3 or 3* (e.g., chiral ligand 17) may account for the increased reaction conversion and enantioselectivity when compared to the monocyclic and less basic chiral ligands L2, L3, L4, L5, L7, and L10.

Example 1

Preparation of Ethyl 2-(5-bromopyridin-2-yl)-2,2-difluoroacetate (15-Br)

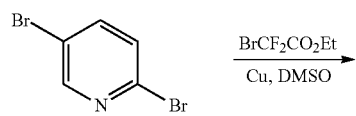

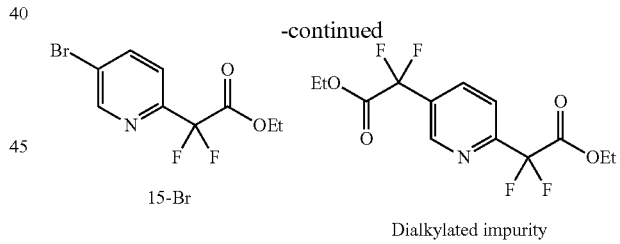

Dialkylated impurity

In a clean multi-neck round bottom flask, copper powder (274.7 g, 2.05 eq) was suspended in dimethyl sulfoxide (3.5 L, 7 vol) at 20-35° C. Ethyl bromodifluoroacetate (449 g, 1.05 eq) was slowly added to the reaction mixture at 20-25° C. and stirred for 1-2 h. 2, 5-Dibromopyridine (500 g, 1 eq) was added to the reaction mixture and the temperature was increased to 35-40° C. The reaction mixture was maintained at this temperature for 18-24 h and the reaction progress was monitored by GC.

After completion of the reaction, ethyl acetate (7 L, 14 vol) was added to the reaction mixture and stirring was continued for 60-90 min at 20-35° C. The reaction mixture was filtered through a Celite bed (100 g; 0.2 times w/w Celite and 1 L; 2 vol ethyl acetate). The reactor was washed with ethyl acetate (6 L, 12 vol) and the washings were filtered through a Celite bed. The Celite bed was finally washed with ethyl acetate (1 L, 2 vol) and all the filtered mother liquors were combined. The pooled ethyl acetate solution was cooled to 8-10° C., washed with the buffer solution (5 L, 10 vol) below 15° C. (Note: The addition of buffer solution was exothermic in nature. Controlled addition of buffer was required to maintain the reaction mixture temperature below 15° C.). The ethyl acetate layer was washed again with the buffer solution until (7.5 L; 3×5 vol) the aqueous layer remained colorless. The organic layer was washed with a 1:1 solution of 10% w/w aqueous sodium chloride and the buffer solution (2.5 L; 5 vol). The organic layer was then transferred into a dry reactor and the ethyl acetate was distilled under reduced pressure to provide crude 15-Br.

The crude 15-Br was purified by high vacuum fractional distillation and the distilled fractions having 15-Br purity greater than 93% (with the dialkylated not more than 2% and starting material less than 0.5%) were pooled together to afford 15-Br.

Yield after distillation: 47.7% with >93% purity by GC (pale yellow liquid). Another 10% yield was obtained by re-distillation of impure fractions resulting in overall yield of ~55-60%.

$^1$H NMR: δ values with respect to TMS (DMSO-$d_6$; 400 MHz): 8.85 (1H, d, 1.6 Hz), 8.34 (1H, dd, J=2.0 Hz, 6.8 Hz), 7.83 (1H, d, J=6.8 Hz), 4.33 (2H, q, J=6.0 Hz), 1.22 (3H, t, J=6.0 Hz). $^{13}$C NMR: 162.22 (t, —C=O), 150.40 (Ar—C—), 149.35 (t, Ar—C), 140.52 (Ar—C), 123.01 (Ar—C), 122.07 (Ar—C), 111.80 (t, —CF$_2$), 63.23 (—OCH$_2$—), 13.45 (—CH$_2$CH$_3$).

Example 2

Preparation of 2-(5-bromopyridin-2-yl)-1-(2,4-difluorophenyl)-2,2-difluoroethanone (16-Br)

A. One-step Method

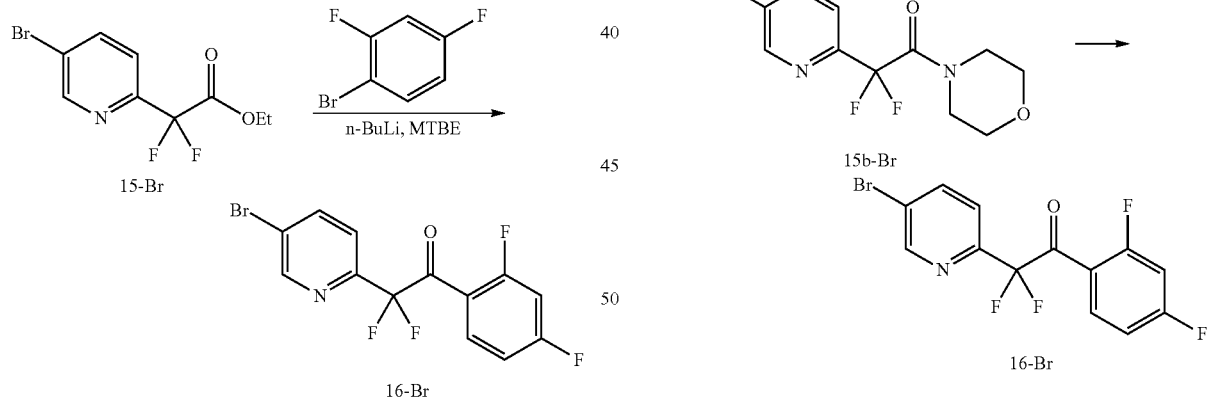

1-Bromo-2,4-difluorobenzene (268.7 g; 1.3 eq) was dissolved in methyl tert butyl ether (MTBE, 3.78 L, 12.6 vol) at 20-35° C. and the reaction mixture was cooled to −70 to −65° C. using an acetone/dry ice bath. n-Butyl lithium (689 mL, 1.3 eq; 2.5 M) was then added to the reaction mixture maintaining the reaction temperature below −65° C. (Note: Controlled addition of the n-Butyl Lithium to the reaction mixture was needed to maintain the reaction mixture temperature below −65° C.). After maintaining the reaction mixture at this temperature for 30-45 min, 15-Br (300 g, 1 eq) dissolved in MTBE (900 mL, 3 vol) was added to the reaction mixture below −65° C. The reaction mixture was continued to stir at this temperature for 60-90 min and the reaction progress was monitored by GC.

The reaction was quenched by slow addition of a 20% w/w ammonium chloride solution (750 mL, 2.5 vol) below −65° C. The reaction mixture was gradually warmed to 20-35° C. and an additional amount of a 20% w/w ammonium chloride solution (750 mL, 2.5 vol) was added. The aqueous layer was separated, the organic layer was washed with a 10% w/w sodium bicarbonate solution (600 mL, 2 vol) followed by a 5% sodium chloride wash (600 mL, 2 vol). The organic layer was dried over sodium sulfate (60 g; 0.2 times w/w), filtered and the sodium sulfate was washed with MTBE (300 mL, 1 vol). The organic layer along with washings was distilled below 45° C. under reduced pressure until no more solvent was collected in the receiver. The distillation temperature was increased to 55-60° C., maintained under vacuum for 3-4 h and cooled to 20-35° C. to afford 275 g (73.6% yield, 72.71% purity by HPLC) of 16-Br as a pale yellow liquid.

$^1$H NMR: δ values with respect to TMS (DMSO-$d_6$; 400 MHz): 8.63 (1H, d, 1.6 Hz, Ar—H), 8.07-8.01 (2H, m, 2×Ar—H), 7.72 (1H, d, J=6.8 Hz, Ar—H), 7.07-6.82 (1H, m, Ar—H), 6.81-6.80 (1H, m, Ar—H).

$^{13}$C NMR: 185.60 (t, —C=O), 166.42 (dd, Ar—C—), 162.24 (dd, Ar—C), 150.80 (Ar—C), 150.35 (Ar—C), 140.02 (Ar—C), 133.82 (Ar—C), 123.06 (Ar—C), 1122.33 (Ar—C), 118.44 (Ar—C), 114.07 (—CF$_2$—), 122.07 (Ar—C), 105.09 (Ar—C).

B. Two-Step Method Via 15b-Br

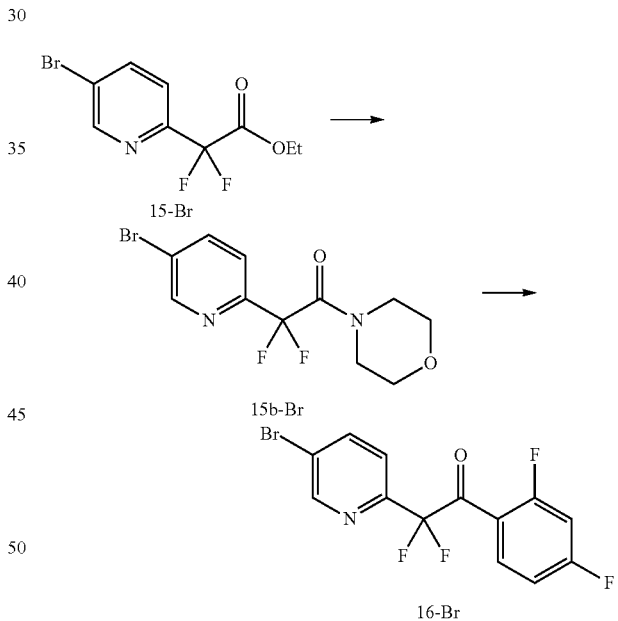

15-Br (147.0 g) was dissolved in n-heptane (1.21 L) and transferred to a 5-L reactor equipped with overhead stirrer, thermocouple, condenser and addition funnel. Morpholine (202 ml) was added. The solution was heated to 60° C. and stirred overnight. The reaction was complete by HPLC analysis (0.2% 15-Br; 94.7% 15b-Br). The reaction was cooled to room temperature and 1.21 L of MTBE was added. The solution was cooled to ~4° C. and quenched by slow addition of 30% citric acid (563 ml) to maintain the internal temperature <15° C. After stirring for one hour, the layers were allowed to settle and were separated (Aq. pH=5). The organic layer was washed with 30% citric acid (322 ml) and 9% NaHCO$_3$ (322 ml, aq. pH 7+ after separation). The organic layer was concentrated on the rotary evaporator to 454 g (some precipitation started immediately and increased during concentration). After stirring at room temperature the suspension was filtered and the product cake was washed with n-heptane (200 ml). The solid was dried in a vacuum oven at room temperature to provide 129.2 g (77%) dense powder. The purity was 96.5% by HPLC analysis.

To a 1-L flask equipped with overhead stirring, thermocouple, condenser and addition funnel was added magnesium turnings (14.65 g), THF (580 ml) and 1-bromo-2,4-difluorobenzene (30.2 g, 0.39 equiv). The mixture was stirred until the reaction initiated and self-heating brought the reaction temperature to 44° C. The temperature was controlled with a cooling bath as the remaining 1-bromo-2,4-difluorobenzene (86.1 g, 1.11 equiv) was added over about 30 min. at an internal temperature of 35-40° C. The reaction was stirred for 2 hours while gradually cooling to room temperature. The dark yellow solution was further cooled to 12° C.

During the Grignard formation, a jacketed 2-L flask equipped with overhead stirring, thermocouple, and addition funnel was charged with morpholine amide 15b-Br (129.0 g) and THF (645 ml). The mixture was stirred at room temperature until the solid dissolved, and then the solution was cooled to −8.7° C. The Grignard solution was added via addition funnel over about 30 min. at a temperature of −5 to 0° C. The reaction was stirred at 0° C. for 1 hour and endpointed by HPLC analysis. The reaction mixture was cooled to −5° C. and quenched by slow addition of 2N HCl over 1 hour at ≤10° C. The mixture was stirred for 0.5 h then the layers were allowed to settle and were separated. The aqueous layer was extracted with MTBE (280 ml). The combined organic layers were washed with 9% NaHCO$_3$ (263 g) and 20% NaCl (258 ml). The organic layer was concentrated on the rotary evaporator with THF rinses to transfer all the solution to the distillation flask. Additional THF (100 ml) and toluene (3×100 ml) were added and distilled to remove residual water from the product. After drying under vacuum, the residue was 159.8 g of a dark brown waxy solid (>theory). The purity was approximately 93% by HPLC analysis.

Grignard Formation/Coupling Reaction 2:

Magnesium (0.022 kg, 0.903 mol), 1-bromo-2,4-difluorobenzene (0.027 kg, 0.14 mol) and tetrahydrofuran (THF) (1.4 L) were charged to a 2 L reactor fitted with a nitrogen inlet/outlet, 0.25 L dropping funnel, temperature probe and reflux condenser. After stirring for ca. 40 min at 22° C., the reaction initiated and was allowed to reach 35° C. Cooling was applied and further 1-bromo-2,4-difluorobenzene (0.153 kg, 0.79 mol) was added at 35-40° C. over 0.5 hr. On completion of the addition, the reaction was stirred at 35-40° C. for a further 1 h before cooling solution of the Grignard reagent to 20-25° C. over 1 hr. During the 1 hr cooling period, 15b-Br (0.2 kg, 0.62 mol) and THF (0.8 L) were charged to a 5 L reactor fitted with a nitrogen inlet/outlet, 0.5 L dropping funnel, temperature probe and reflux condenser and stirred at 15-20° C. to give a solution before cooling to −5 to 0° C.

The Grignard reagent was added to the solution of morpholine amide in THF at −3 to 2° C. over 50 min and the solution stirred at approximately 0° C. for 1 hr. A sample of the reaction mixture was submitted for GC analysis. A 1 ml sample was quenched into 2 M hydrochloric acid solution (5 ml) and extracted with MTBE (2 ml). The organic layer was submitted for analysis, which indicated 0.76% morpholine amide remaining.

The reaction was quenched by the addition of a 2 M hydrochloric acid solution (1 L) over 0.75 hr at less than 10° C. and stirred for a further 0.5 hr. Stirring was stopped and the phases allowed to separate. The lower aqueous layer was removed and extracted with tert-butylmethyl ether (MTBE) (0.4 L). The combined organic layers were washed with a saturated sodium hydrogen carbonate solution (0.4 L) and a saturated sodium chloride solution (0.4 L). The solvent was evaporated under vacuum at less than 50° C. and co-distilled with portions of toluene (0.2 L) until the water content by Karl Fischer (KF) analysis was less than 0.1%.

Toluene (0.37 L) and n-heptane (0.37 L) were added to the residue together with SilicaFlash P60 (40-63 micron) (0.11 kg), and the reaction stirred at 20-25° C. for 1 hr. The reaction was filtered and washed with toluene/n-heptane (1:1) (2 L). The solvent was evaporated at <50° C. and solvent swapped into THF to give an approximately 36 wt % solution of 16-Br. Gravimetric analysis of a sample of the toluene/n-heptane solution prior to evaporation indicated a mass yield of 0.21 kg (98.5%). GC assay of this material was 95.34%, to give a contained yield of 93.9%. GC (AUC) analysis of an evaporated sample was 94.5%, and HPLC (AUC) was 97.1%.

Example 3

Preparation of 1-(5-bromopyridin-2-yl)-2-(2,4-difluorophenyl)-1,1-difluoro-3-nitropropan-2-ol (1-Br or 1*-Br)

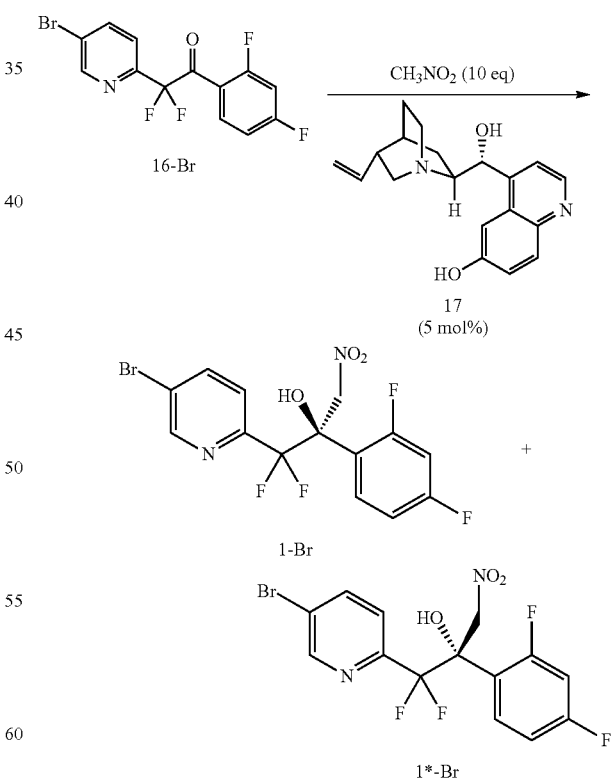

A reaction flask was charged with 16-Br (1.3 g, 3.7 mmol, 1.0 eq) and THF (3.3 mL) yielding a yellow solution. The organocatalyst 17 (59 mg, 0.19 mmol, 0.05 eq), prepared according to *J. Am. Chem. Soc.* 2012, 164, 169-172, was added to the mixture and the contents were cooled to 5° C. Subsequently, nitromethane (2.0 mL, 2.27 g, 37 mmol 10 eq) was added and the mixture was stirred at 5° C. for 23.5 h. At this point, an HPLC sample was taken to determine conversion (>95% conversion) and enantiomeric ratio (ca. 90:10 1-Br:1*-Br). For the work up, the mixture was diluted with ethyl acetate (12 mL) and an aqueous solution of acetic acid (acetic acid 0.6 ml and water 10 ml) was added. The phases were separated and the organic phase was washed with water (8 mL) and brine (8 mL). The volatiles were removed under reduced pressure to obtain 1.15 g (75% yield) of the crude product.

$^1$H NMR: δ values with respect to TMS (DMSO-$d_6$; 400 MHz): 8.59 (1H, d, J=2.0 Hz), 7.92 (1H, dd, J=8.4 Hz, 2.3 Hz), 7.45 (1H, m), 7.34 (1H, dd, J=8.4 Hz, 2.3 Hz), 6.86-6.75 (2H, m), 5.70 (1H, d, J=12.8 Hz), 5.16 (1H, d, J=12.8 Hz).

Chiral HPLC: Retention Times: 10.97 min (1*-Br); 14.82 min (1-Br)

| HPLC Set up | |
|---|---|
| HPLC column | Chiralpak AD-H 250 mm × 4.6 mm × 5 μm |
| Column temperature | 25° C. |
| Sample temperature | 25° C. |
| Flow rate | 0.8 mL/min |
| Injection Volume | 3 μL |
| Wavelength | 215 nm |
| Run time | 20 min |
| Mobile Phase | 90 vol % n-hexane + 10 vol % 2-PrOH (isocratic) |

Example 4

Preparation of 3-amino-1-(5-bromopyridin-2-yl)-2-(2,4-difluorophenyl)-1,1-difluoropropan-2-ol (11-Br or 11*-Br)

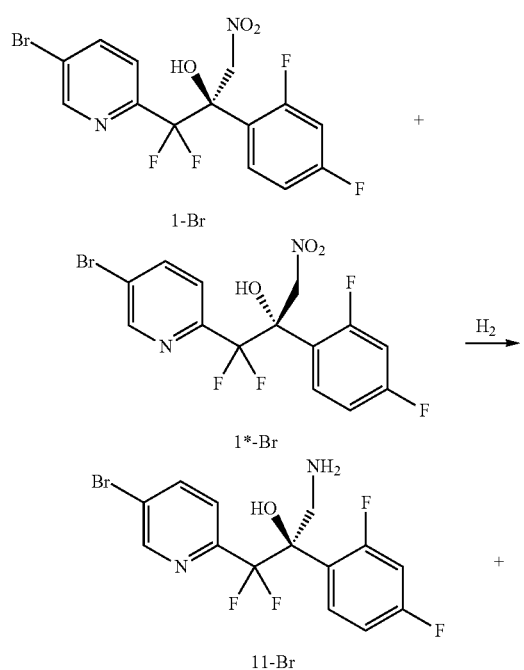

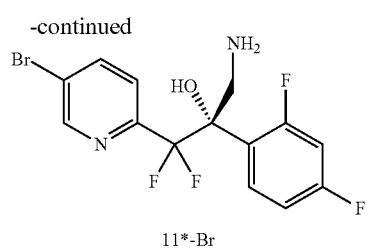

A chamber of a screening autoclave was charged with 1-Br/1*-Br (150 mg, 0.366 mmol), Noblyst® P8071[1] (ca. 0.40 mol % Pt relative to 1-Br/1*-Br) and MeOH (1.5 mL). The chamber was flushed several times with $H_2$ and pressurized to 4 bar. After 16 h, a sample was analyzed by HPLC. Upon reaction completion, the reaction mixture was filtered through a glass filter and the solvent was removed under reduced pressure to obtain the crude product.

$^1$H NMR: δ values with respect to TMS (CDCl$_3$; 400 MHz): 8.59 (1H, d, J=2.1 Hz), 7.83 (1H, dd, J=8.4 Hz, 2.2 Hz), 7.43 (1H, m), 7.24 (1H, d, J=8.4 Hz), 6.80-6.67 (2H, m), 5.20 (2H, s), 3.89 (1H, d, J=14.2 Hz), 3.47 (1H, d, J=14.2 Hz).

Achiral HPLC: Retention Times: 7.25 min (11-Br/11*-Br)

| HPLC Set up | |
|---|---|
| HPLC column | Waters × Bridge Shield RP 18 150 mm × 4.6 mm 3.5 μm |
| Column temperature | 25° C. |
| Sample temperature | 25° C. |
| Flow rate | 0.8 mL/min |
| Injection Volume | 3 μL |
| Wavelength | 254 nm |
| Run time | 18 min |
| Mobile Phase A | Water + 0.1% TFA |
| Mobile Phase B | Acetonitrile + 0.1% TFA |

| Gradient | | |
|---|---|---|
| t [min] | Mobile Phase A [vol %] | Mobile Phase B [vol %] |
| 0 min | 96 | 4 |
| 20 min | 4 | 96 |

Enantioenrichment of 11-Br/11*-Br

Di-p-toluoyl-L-tartaric acid (0.069 kg, 0.178 ml; 0.3 eq.) was charged under nitrogen to a 5 L reactor equipped with a nitrogen inlet/outlet. A solution of 11-Br/11*-Br in isopropyl alcohol (IPA, 1.718 kg; contained mass 0.225 kg, 0.59 mol; 1 eq.) was added, followed by acetonitrile (0.35 kg). The reaction mixture was stirred at approximately 20° C. and a solution resulted. The reaction was heated to 50-55° C. (target 52° C.) and stirred at this temperature for 4 hr, during which time a precipitate resulted. An in-process chiral HPLC sample of the reaction was taken by hot filtration of the sample and washing with IPA/acetonitrile (4:1). This indicated a chiral purity of >99%.

The reaction was allowed to cool and stir at 20-25° C. over 16 hr. A second sample was submitted for chiral HPLC analysis, which was 99.5%. The reaction mixture was filtered and washed with a mixture of IPA/acetonitrile (4:1) (0.84 L). The resulting solid was dried under vacuum at 50° C. to give 11-Br hemi L-DTTA salt (0.113 kg) as a white solid. The mass yield was 33.2%, which is 66.35% of the desired isomer. Chiral HPLC was 99.6%, and achiral HPLC was 99.7%.

Neutralization of 11-Br Hemi L-DTTA Salt

11-Br hemi L-DTTA salt (250 g, 0.437 mol) was charged to a 3-necked flask equipped with overhead stirrer, nitrogen inlet, dropping funnel and thermocouple. The solid was suspended in MTBE (1.25 L). A 10% $K_2CO_3$ aq. solution was added slowly at room temperature (slightly exothermic) with stirring. After complete addition, the biphasic mixture was stirred for 10 minutes until all solid dissolved. The aqueous layer was separated and extracted with another 0.625 L of MTBE. The combined organic layers were concentrated on a rotary evaporator under vacuum. The residue was diluted in toluene (0.30 L) and concentrated again to provide a syrup residue of 11-Br (169.7 g). The procedure was repeated twice more starting with 250 g and 243 g, respectively, of 11-Br hemi L-DTTA salt.

Example 5

Preparation of 1-(5-bromopyridin-2-yl)-2-(2,4-difluorophenyl)-1,1-difluoro-3-(1H-tetrazol-1-yl)propan-2-ol (13-Br or 13*-Br)

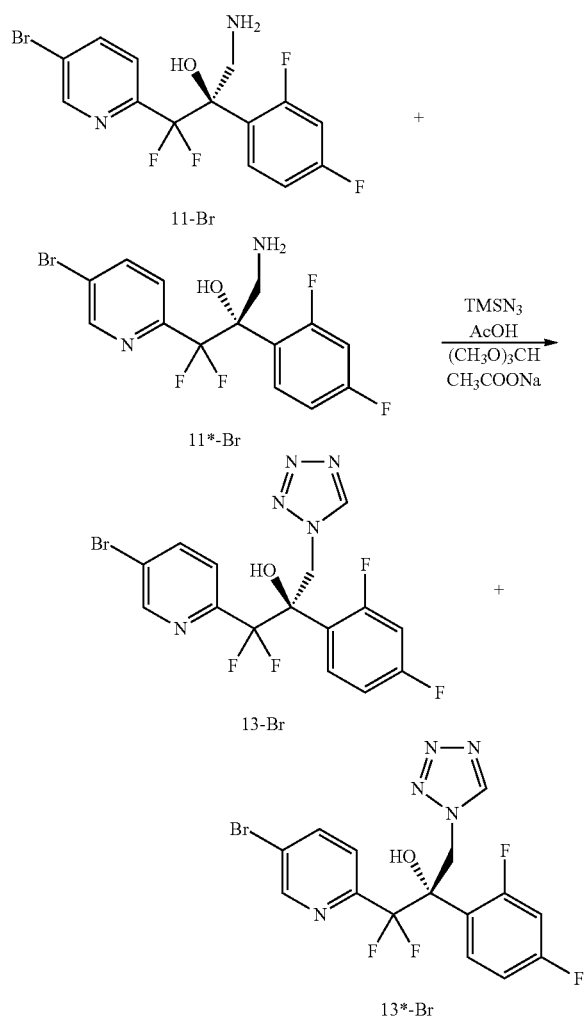

11-Br/11*-Br (20.0 g, 1 eq.) was added to acetic acid (50 mL, 2.5 vol) at 25-35° C. followed by the addition of anhydrous sodium acetate (4.32 g, 1 eq) and trimethyl orthoformate (15.08 g, 2.7 eq). The reaction mixture was stirred for 15-20 min at this temperature and trimethylsilyl azide (12.74 g, 2.1 eq) was added to the reaction mixture (Chilled water was circulated through the condenser to minimize the loss of trimethylsilyl azide from the reaction mixture by evaporation). The reaction mixture was then heated to 70-75° C. and maintained at this temperature for 2-3 h. The reaction progress was monitored by HPLC. Once the reaction was complete, the reaction mixture was cooled to 25-35° C. and water (200 mL, 10 vol) was added. The reaction mixture was extracted with ethyl acetate (400 mL, 20 vol) and the aqueous layer was back extracted with ethyl acetate (100 mL, 5 vol). The combined organic layers were washed with a 10% potassium carbonate solution (3×200 mL; 3×10 vol) followed by a 10% NaCl wash (1×200 mL, 10 vol). The organic layer was distilled under reduced pressure below 45° C. The crude product obtained was azeotroped with heptanes (3×200 mL) to provide 21.5 g (94% yield, 99.26% purity) of the tetrazole 13-Br/13*-Br compound as a pale brown solid (low melting solid).

$^1$H NMR: δ values with respect to TMS (DMSO-$d_6$; 400 MHz NMR instrument): 9.13 (1H, Ar—H), 8.74 (1H, Ar—H), 8.22-8.20 (1H, m, Ar—H), 7.44 (1H, d, J=7.2 Hz, Ar—H), 7.29 (1H, Ar—H), 7.23-7.17 (1H, m, Ar—H), 6.92-6.88 (1H, Ar—H), 5.61 (1H, d, J=11.2 Hz, —OCH$_A$H$_B$—), 5.08 (1H, d, J=5.6 Hz, —OCH$_A$H$_B$—).

$^{13}$C NMR: 163.67-161.59 (dd, Ar—C—), 160.60-158.50 (dd, Ar—C—), 149.65 (Ar—C), 144.99 (Ar—C), 139.75 (Ar—C), 131.65 (Ar—C), 124.26 (Ar—C), 122.32 (d, Ar—C), 119.16 (t, —CF$_2$—), 118.70 (d, Ar—C), 111.05 (d, Ar—C) 104.29 (t, Ar—C), 76.79 (t, —C—OH), 59.72 (Ar—C), 50.23 (—OCH$_2$N—).

Alternative Procedure for the Synthesis of 13-Br/13*-Br

11-Br/11*-Br (76.6 g, theoretically 33.1 g contained 11-Br, 87.4 mmol) was transferred to a pressure bottle. Glacial acetic acid (117 g, 0.1% water by KF analysis), sodium acetate (7.18 g, 87.6 mmol, 1 equiv, 0.44% water by KF analysis), and trimethylorthoformate (55.75 g, 525 mmol, 6 equiv, 0.02% water by KF analysis) were added and the mixture was stirred under nitrogen at room temperature for 2 hours (during this time trimethylorthoformate reacts off any residual moisture in the system prior to starting the reaction). Trimethylsilyl azide (18.5 ml, 131 mmol, 1.5 equiv) was added all at once. The pressure bottle was sealed and heated in an oil bath at 67° C. overnight (16 h), then cooled and sampled for completion (No 11-Br/11*-Br was detected. The expected byproduct of an incomplete reaction, the formamide of 11-Br/11*-Br, if present, was very small). The reaction mixture was diluted with 2-MeTHF (332 ml) and a total of 312 ml of water (232 mL of water was added initially, and later 80 mL was added when some precipitate formed, presumably sodium acetate, during the cold neutralization). The mixture was cooled to 0° C. and neutralized by slow addition of 50% NaOH (exothermic, added at a rate to maintain the internal temperature <25° C.). A total of 177 g 50% NaOH brought the pH to 10. After warming to 25° C. the layers were settled and separated. The organic product phase was washed with 10% aqueous potassium carbonate (181 g)—Aq. pH=>10. The organic layer was washed with 20% aqueous sodium chloride (191 g)—Aq. pH=≥7.

For scale up, the organic layer can be concentrated under vacuum and dried by additional distillations of 2-MeTHF with a final target volume of 5 mL 2-MeTHF per gram theoretical 13-Br/13*-Br and target water content <0.1%. During the distillations the solution was polish-filtered to remove a small amount of inorganic solid that was observed.

Example 6

Preparation of 4-((4-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (5 or 5*)

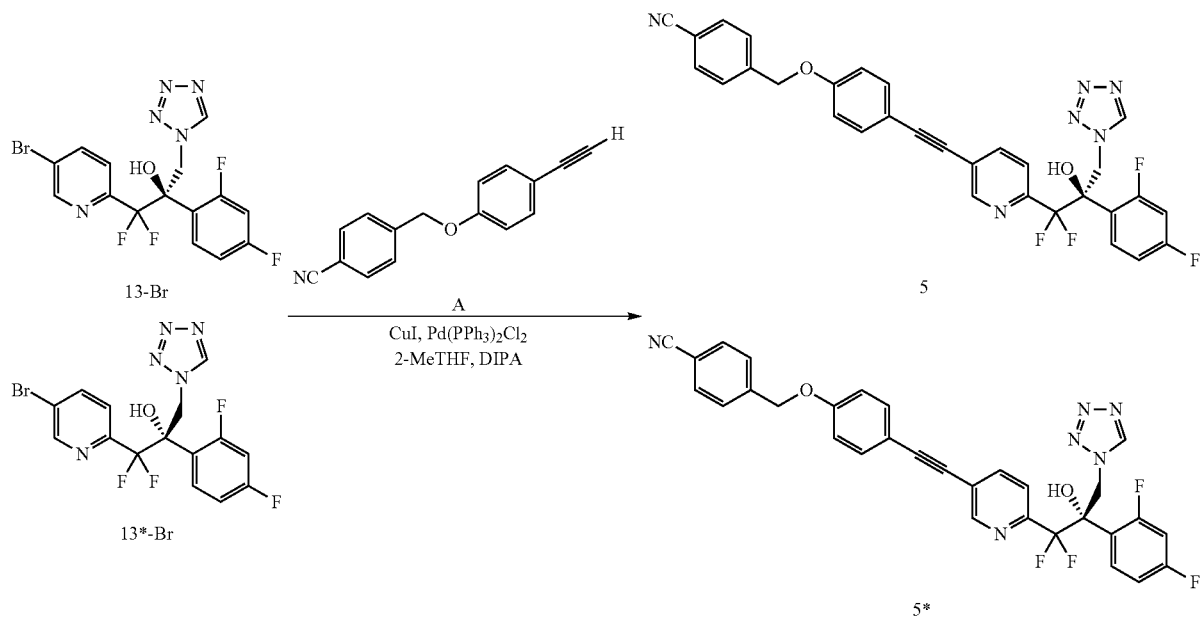

To a round bottom flask equipped with overhead stirrer, dropping funnel, nitrogen inlet and thermocouple was charged 13-Br/13*-Br (47.4 g, 110 mmol, 1 equiv.). A total of 237 ml of 2-MeTHF (5 vol) was added to dissolve and transfer the residue to the reaction flask. Diisopropylamine (236 ml, 5 vol), compound A (27.38 g, 117.4 mmol, 1.07 equiv.) and CuI (0.21 g, 1.1 mmol, 1 mol %) were added. The mixture was sparged with nitrogen for 11 min. Pd(PPh$_3$)$_2$Cl$_2$ (0.385 g, 0.5 mol %) was added, and the mixture was again sparged with nitrogen for 6 minutes. The reaction mixture was heated to 50° C. and stirred overnight. After 24 h the reaction was complete by HPLC analysis as described in the table below.

| Time | 13-Br/13*-Br (A %) | compound A (A %) | 5/5* (A %) |
|---|---|---|---|
| 4 h | 4.1 | 3.3 | 90.4 |
| 8 h | 2.0 | 1.5 | 93.6 |
| 24 h | 0.8 | 1.2 | 95.8 |

The reaction mixture was cooled to room temperature. Celite 545 (5.2 g) was added, followed by slow addition of water (237 mL, 5 vol) and the biphasic mixture was stirred for ½ hour. The mixture was filtered with a rinse of 2-MeTHF (50 mL, 1 vol) and the layers were settled. The aqueous layer (241 g, pH 11-12) was removed. The upper product layer was diluted with 2-MeTHF (200 mL, 4 vol) and stirred with a 10% aqueous solution of disodium EDTA dihydrate (247 g) for 5 hours at room temperature. The layers were settled and separated (aqueous 254 g, pH 12, blue in color). The upper organic layer was stirred with 10% aqueous N-acetyl cysteine solution (237 mL) at 50° C. for 22 h. After cooling to room temperature, the layers were settled (slow) and separated. The aqueous layer was drained (287 g, pH 10-11). The upper organic layer was stirred again with 10% aqueous N-acetyl cysteine solution (238 g) at 50° C. for 22 h. After cooling to room temperature, the layers were settled (slow) and separated. The aqueous layer was removed (277 g, pH 10).

The resulting dark amber organic layer (460 g) was sampled for Pd and Cu analysis (results in the table below) and concentrated to about ½ volume. 2-MeTHF was added and concentrated to about ½ volume. 2-MeTHF was added again and concentrated to 295 g solution. A total of about 482 g of solvent was removed by distillation. The water content of the final solution was 0.55% by KF analysis. NMR analysis indicated that the majority of diisopropylamine was removed.

The solution was divided into two equal portions. One-half was treated with SSI Si-DMT metal scavenger (3.2 g, 10% based on theoretical yield of 5/5*) and Darco G-60 carbon (6.4 g, 20% based on theoretical yield of 5/5*). The other half was treated with Phosphonics STA3 metal scavenger (3.2 g) and Darco G-60 carbon (6.4 g). Both portions were stirred at 50° C. for 20-21 hours. Both portions were then separately filtered through a glass fiber filter and a 1 micron PTFE membrane with 2-MeTHF rinses (about 35 g each). Both filtrates were sampled for Pd and Cu analysis ((results in the table below).

| Sample | Cu (ppm) | Pd (ppm) |
|---|---|---|
| After N-Acetyl cysteine washes | <3.7 | 287 |
| SSI Si-DMT + Darco treatment | <3.7 | 49 |
| Phosphonics STA3 + Darco treatment | <2.5 | 70 |

The filtrates were combined for a total of 345 g solution. The solution was partially concentrated and solvent exchanged into toluene with repeated additions of toluene (total 643 g) and partial concentration to a final toluene solution weight of 268.5 g (theoretically 64.1 g of 5/5* and 236 mL of toluene). NMR analysis indicated no diisopropylamine remained and about 1% of 2-MeTHF)

The mixture was allowed to crystallize while stirring overnight. The suspension was heated to 55-60° C. until a very thin suspension remained and then was slow cooled at 1° C./h overnight (If the mixture is cooled too fast, the product may precipitate into a "pudding" consistency. Once a good suspension forms it can be cooled more quickly to isolation temperature). The next day the suspension was cooled in an ice-bath at ca. 10° C. for 3.5 hours. The product was collected on a vacuum filter and rinsed with cold toluene (50 mL in portions). The wet cake was dried in a vacuum oven at 40-50° C. to provide 45.2 g (70.6% overall yield) of 5/5* as a beige-colored powder. The purity was 99.2 A % by the API HPLC analysis method.

Example 7

Preparation of 4-((4-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile 4-methylbenzenesulfonate (14 or 14*)

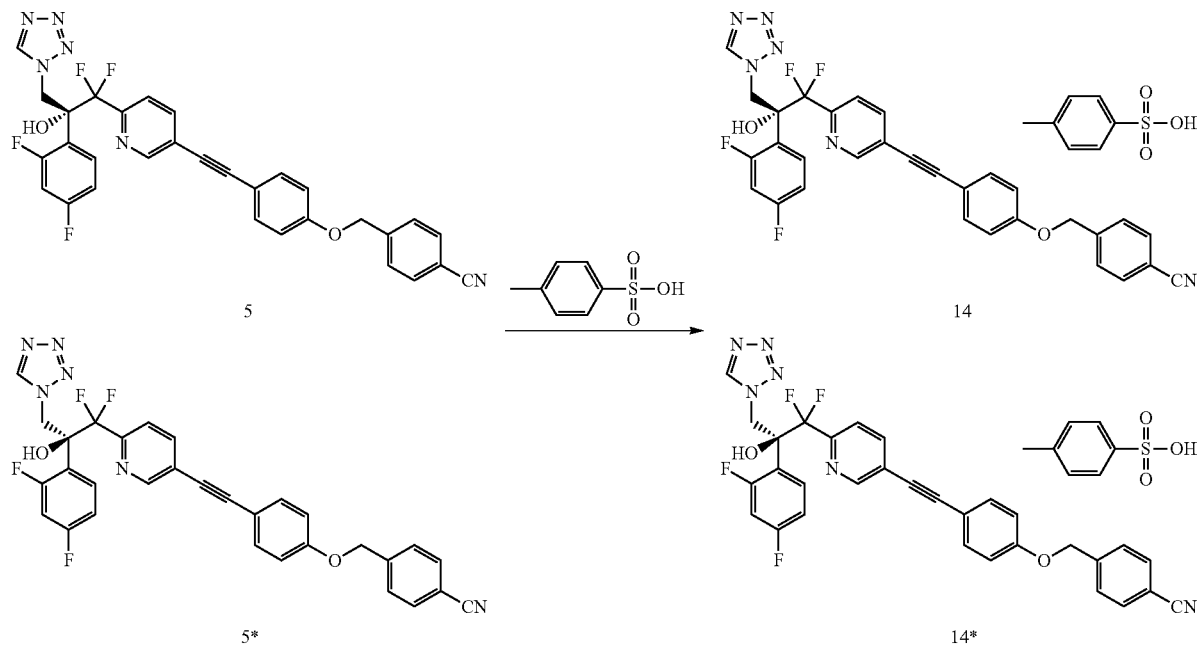

5/5* (15 g, 25.7 mmol) was suspended in isopropyl acetate (120 ml, 8 vol) and warmed to 30° C. para-Toluenesulfonic acid monohydrate (4.88 g, 25.7 mmol, 1 equiv) was added and the mixture was heated to 50-60° C. until a uniform suspension was obtained (Initially a coarse clumpy suspension formed that over time (~1 hr) converted to a uniform suspension of fine particles). The suspension was cooled and stirred overnight at room temperature and then in an ice-bath for several hours. The product was isolated on a vacuum filter and washed with cold isopropyl acetate (15 ml). The wet cake was dried in a vacuum oven at 50° C. to provide 16.7 g (86% yield) of the title compound as a beige powder.

Example 8

Preparation of 4-((4-ethynylphenoxy)methyl)benzonitrile (A)

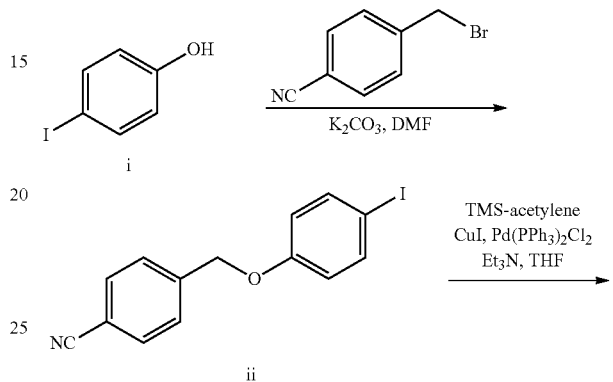

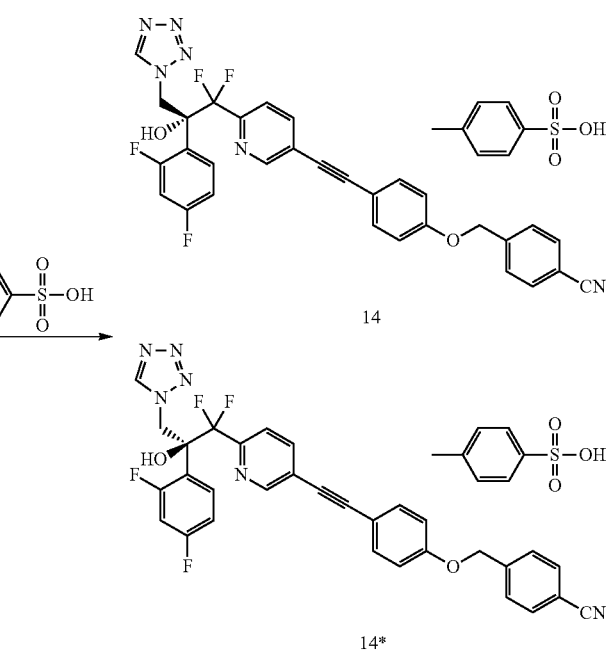

-continued

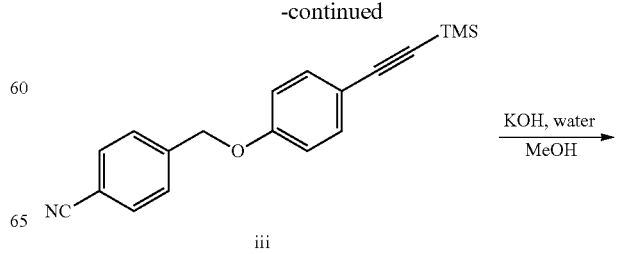

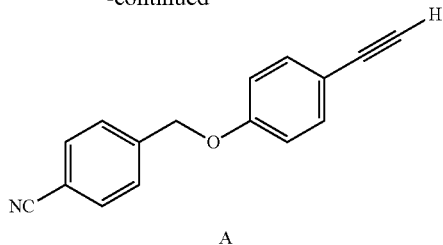

4-((4-Iodophenoxy)methyl)benzonitrile (ii)

4-iodophenol (1.745 kg, 7.93 mol) was charged to a 50-L half-jacketed flask equipped with overhead stirrer, nitrogen inlet, thermocouple and addition funnel. DMF (17.5 L) was added and stirred at 20° C. until all of the solid dissolved. The solution was cooled to −3.5° C. Powdered $K_2CO_3$ (2.18 kg, 15.8 mol, Sigma-Aldrich −325 mesh powder, catalog number 347825) was added and the suspension was stirred vigorously for 3 hours at about −1° C. The mixture was cooled to −2.5° C. and 4-(bromomethyl)benzonitrile (1.48 kg, 7.55 mol) was added. After stirring for 1 hour at about 0° C. the mixture was allowed to warm and stir overnight at 25° C. A sample was taken for analysis. In-process HPLC analysis showed complete disappearance of 4-(bromomethyl)benzonitrile. The reaction mixture was cooled to 10° C. and quenched by slow addition of cold water (18 L) over 25 minutes (maximum temperature was 22° C. during addition). The suspension was stirred for 2 hours at room temperature, then the product was isolated by vacuum filtration and allowed to dry overnight on the vacuum filter (filtrate=38.0 kg). The solid was charged back to the reactor and suspended in deionized water (18 L) for 1.2 hours. The product was isolated by vacuum filtration and allowed to dry on the vacuum filter for 2 hours (filtrate=19.6 kg). (The second vacuum filtration can be replaced by two water washes of 2.5 vol each.) The wet cake (3827 g) was dried in a vacuum oven at 50° C. to a constant weight (4 days) of 2476.5 g (97.9%). The purity was 100 A % by in-process HPLC analysis.

4-((4-ethynylphenoxy)methyl)benzonitrile (A)

4-((4-Iodophenoxy)methyl)benzonitrile (ii) (100 g, 298 mmol) and CuI (571 mg, 1 mol %) were charged to a nitrogen-flushed 3-L round bottom flask equipped with overhead stirrer, addition funnel, nitrogen inlet and thermocouple. Dry THF (500 mL, 5 vol) and triethylamine (204 ml, 2 vol) were added and stirred to form a greenish solution. The solution was cooled to a target of 0° C. Trimethylsilyl acetylene (42.0 g, 428 mmol, 1.43 equiv) was added and the resulting thin greenish suspension was sparged with nitrogen for 11 minutes. $Pd(PPh_3)_2Cl_2$ (421 mg, 0.2 mol %) was added and the mixture was sparged with nitrogen for 10 minutes. The temperature was −7° C. after sparging. The cooling bath was removed and the mixture slowly warmed over 1.3 h to 23.5° C. during which time it became a yellow solution with some suspended solid. The reaction was stirred overnight at this temperature. After 14 h, in-process HPLC analysis showed appearance of 4-((4-((trimethylsilyl)ethynyl)phenoxy)methyl)benzonitrile (iii), and complete disappearance of 4-((4-iodophenoxy)methyl)benzonitrile (ii).

Separately, a solution of 45% KOH (75.0 g, 613 mmol, 2.06 equiv), water (38.1 g) and methanol (310 ml/243 g) was prepared. This solution was cooled to <10° C. and sparged with nitrogen for 14 minutes.

The mixture containing 4-((4-((trimethylsilyl)ethynyl)phenoxy)methyl)benzonitrile (iii) was cooled to 5° C. and the KOH/methanol/water solution was added slowly over 17 minutes to a final temperature of 10° C. The resulting brown thin suspension was allowed to warm and after about 1 hour the reaction was complete by in-process HPLC analysis (0.8% of iii detected). The mixture was cooled and deionized water (866 g total) was added slowly at 10-14° C., resulting in precipitation of A. After 2.8 hours of stirring at reduced temperature, the product was isolated on a vacuum filter (6° C.). The wet cake was washed with 5:1 (v/v) water/THF (2×600 mL) and then water (2×200 mL). The wet cake was dried in a vacuum oven at 40° C. to provide 66.5 g of the title compound as a brown powder (95.5% yield overall from ii). The purity was 99.5 A % by the in-process HPLC method.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A process to prepare a compound of Formula 5 or 5*, or mixture thereof:

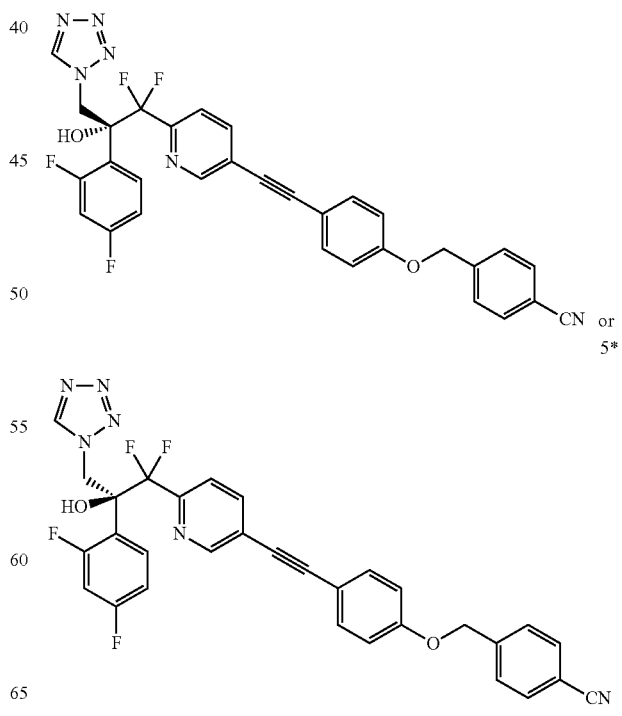

the method comprising at least the initial two steps:
(a) reacting a compound of ketone 6,

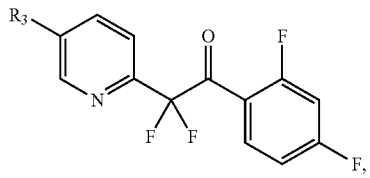

with nitromethane in the presence of a chiral catalyst of Formula 3,

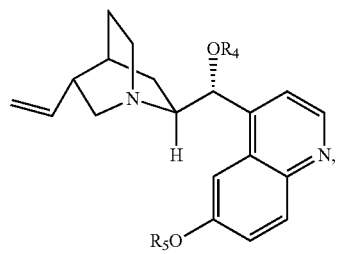

to yield compounds of Formula 7 or 7*,

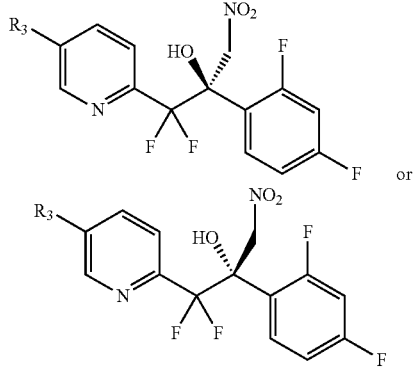

or mixtures thereof; and
(b) reducing compounds of Formula 7 or 7*,

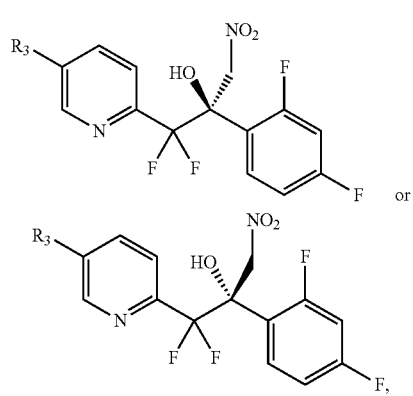

or mixtures thereof to yield compounds of Formula 11 or 11*,

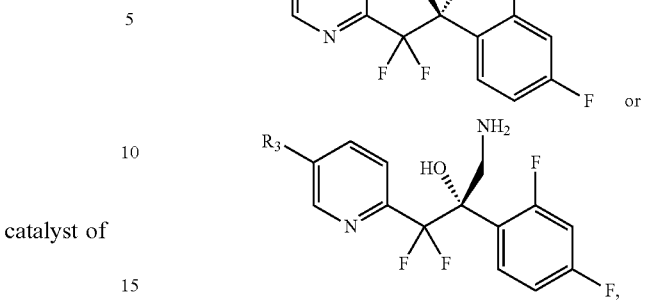

or mixtures thereof;
wherein $R_4$ is H, optionally substituted alkyl, —(C=O)-optionally substituted alkyl, —(C=O)-optionally substituted aryl; and $R_5$ is H, optionally substituted alkyl, optionally substituted arylalkyl, or optionally substituted aryl;

each $R_3$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

2. The process of claim 1, further comprising:
(a) reacting ester 9,

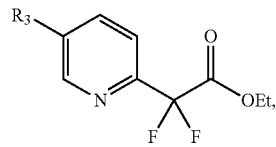

with morpholine
to yield morpholine amide 10

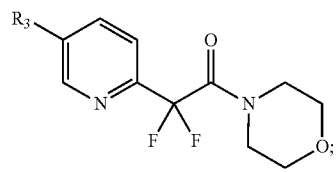

and
(b) arylating of morpholine amide 10,

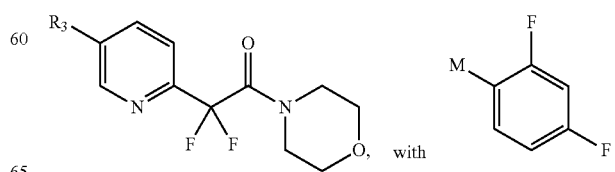

yield ketone 6,

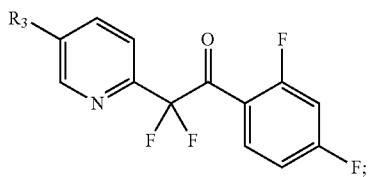

wherein M is Mg, MgX, Li, or AlX₂; and X is halogen, alkyl, or aryl; and each R₃ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

3. The process of claim 2, wherein M is Mg or MgX, and X is halogen.

4. The process of claim 1, further comprising:

(a) alkynylating compounds of Formula 11 or 11*,

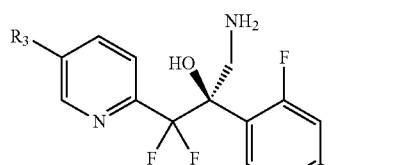

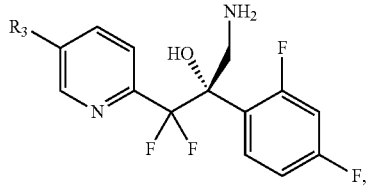

or mixture thereof with an ethynyl moiety R₂,
to yield a compound of Formula 12 or 12*,

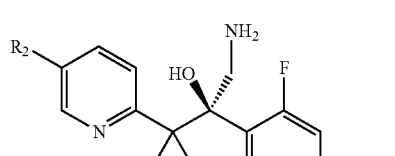

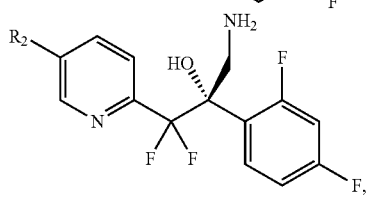

or mixture thereof; and (b) forming the tetrazole of compounds of Formula 12 or 12*,

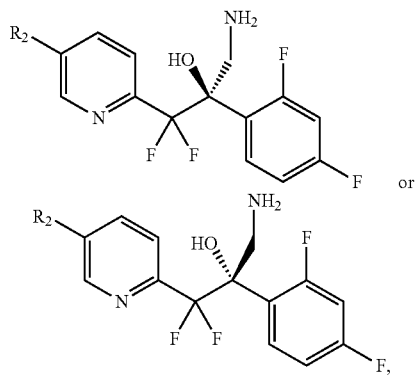

or mixtures thereof, to yield compounds of Formula 18 or 18*,

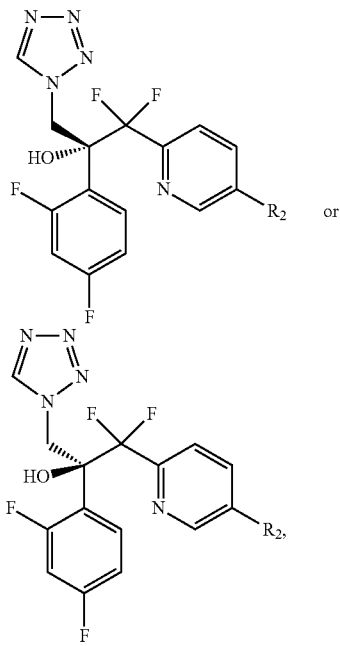

or mixture thereof;

wherein each R₂ is independently ethynyl, substituted ethynyl, or

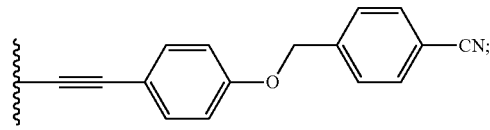 [SMILES: *C#Cc1ccc(OCc2ccc(C#N)cc2)cc1]

and each R₃ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

5. The process of claim 1, further comprising:
(a) forming the tetrazole of compounds of Formula 11 or 11*,

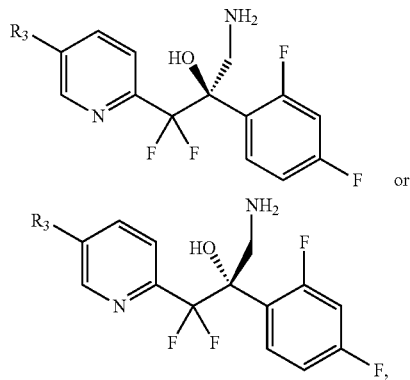

or mixture thereof,
to yield compounds of Formula 13 or 13*,

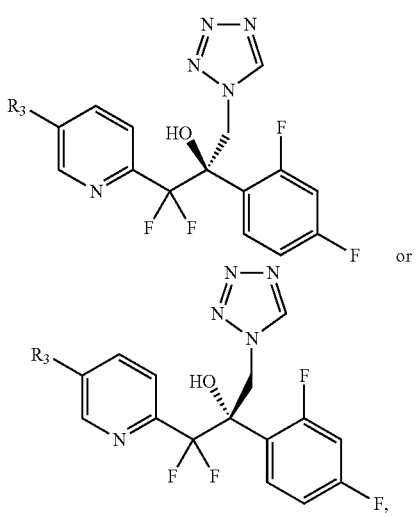

or mixtures thereof; and
(b) alkynylating compounds of Formula 13 or 13*,

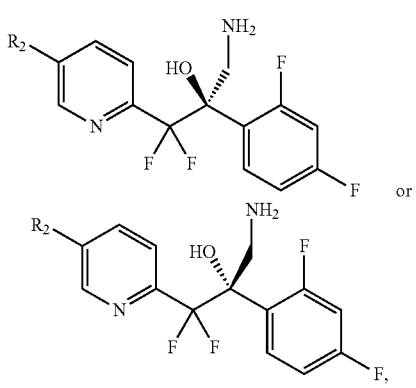

or mixtures thereof, with an ethynyl moiety R₂, to yield compounds of Formula 18 or 18*,

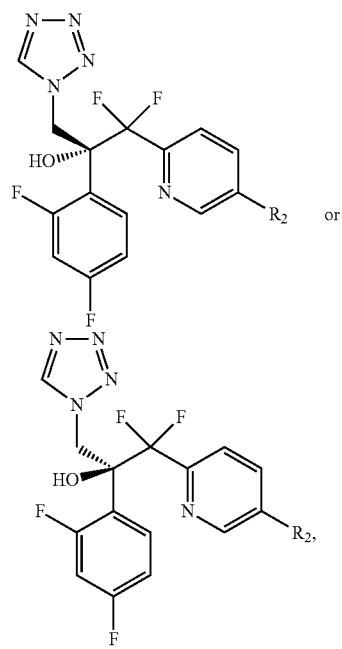

or mixtures thereof;
wherein each $R_2$ is independently ethynyl, substituted ethynyl, or

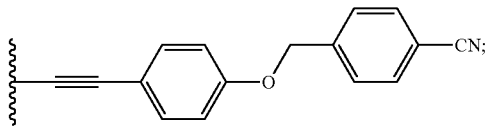 [SMILES: *C#Cc1ccc(OCc2ccc(C#N)cc2)cc1]

and
each $R_3$ is independently halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO₂)-alkyl, —O(SO₂)-substituted alkyl, —O(SO₂)-aryl, or —O(SO₂)-substituted aryl.

6. The process of claim 4, the process further comprising coupling the compound of Formula 18 or 18*, or mixture thereof, wherein $R_2$ is ethynyl, with

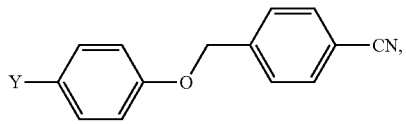

wherein Y is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO₂)-alkyl, —O(SO₂)-substituted alkyl, —O(SO₂)-aryl, or —O(SO₂)-substituted aryl,
to afford of compound of Formula 5 or 5*, or a mixture thereof:

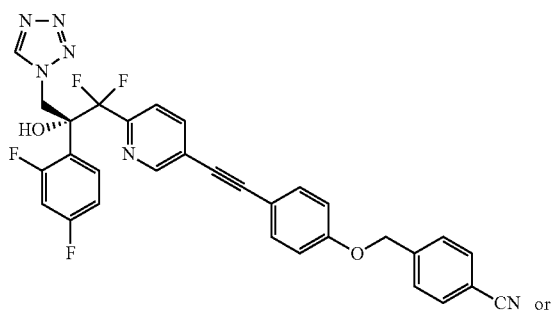

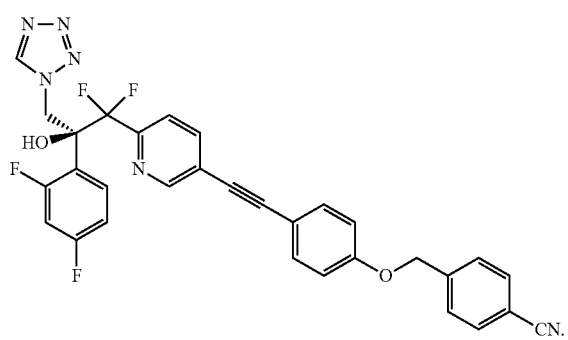

7. The process of claim 5, the process further comprising coupling the compound of Formula 18 or 18*, or mixture thereof, wherein R₂ is ethynyl, with

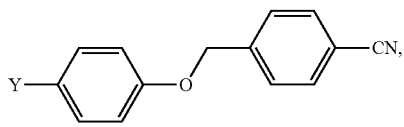

wherein Y is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl, to afford of compound of Formula 5 or 5*, or a mixture thereof:

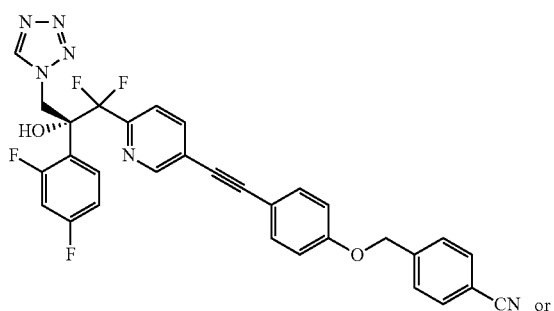

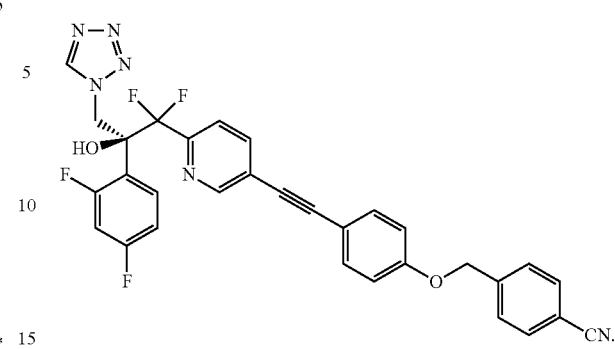

8. The process of claim 4, the process further comprising:
(a) coupling the compound of Formula 18 or 18*, wherein R₂ is ethynyl, with

(b) alkylating the product from step a. with

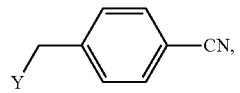

to yield compounds of Formula 5 or 5*, or a mixture thereof:

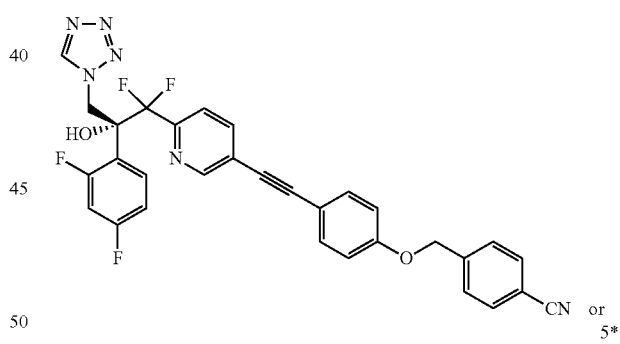

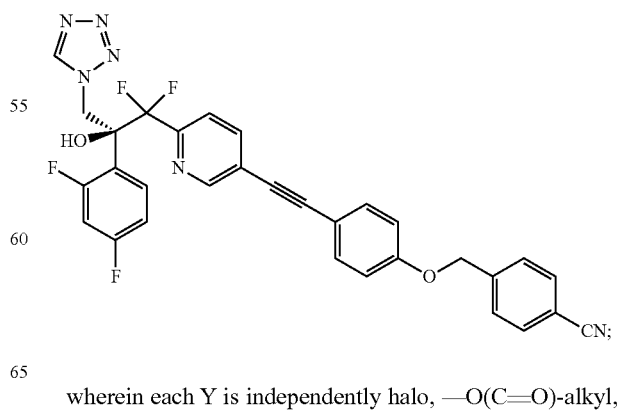

wherein each Y is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

9. The process of claim 5, the process further comprising:

(a) coupling the compound of Formula 18 or 18*, wherein R₂ is ethynyl, with

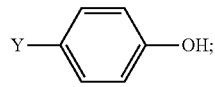

(b) alkylating the product from step a. with

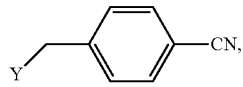

to yield compounds of Formula 5 or 5*, or a mixture thereof:

5

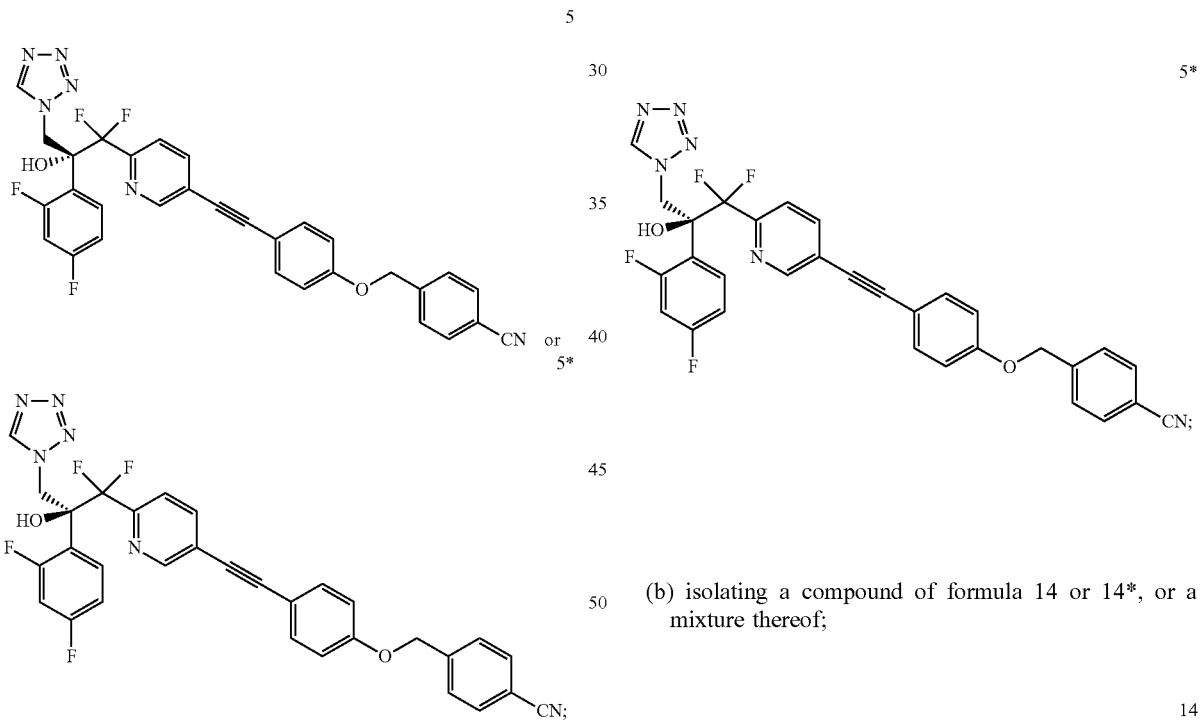

wherein each Y is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

10. The process of claim 4, further comprising:

(a) combining a compound of Formula 5 or 5*, or a mixture thereof, a sulfonic acid

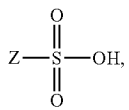

and a crystallization solvent or crystallization solvent mixture; and

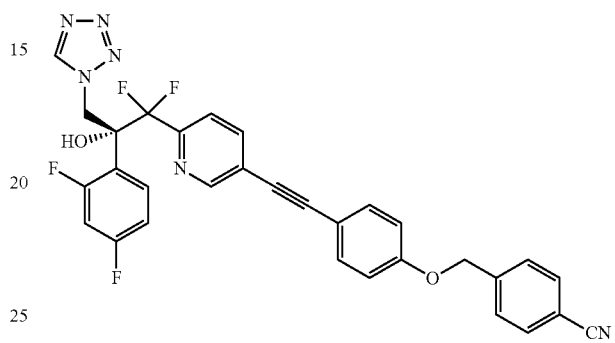

(b) isolating a compound of formula 14 or 14*, or a mixture thereof;

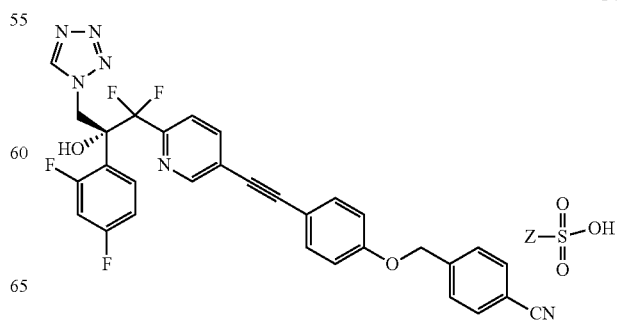

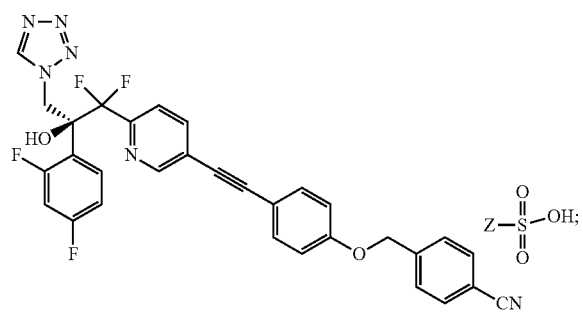

14*

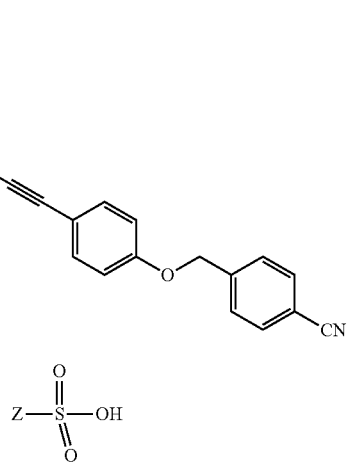

14 wherein each Z is independently aryl, substituted aryl, alkyl, or substituted alkyl.

11. The process of claim 5, further comprising:

(a) combining a compound of Formula 5 or 5*, or a mixture thereof, a sulfonic acid $$Z-\overset{O}{\underset{O}{S}}-OH,$$

and a crystallization solvent or crystallization solvent mixture; and

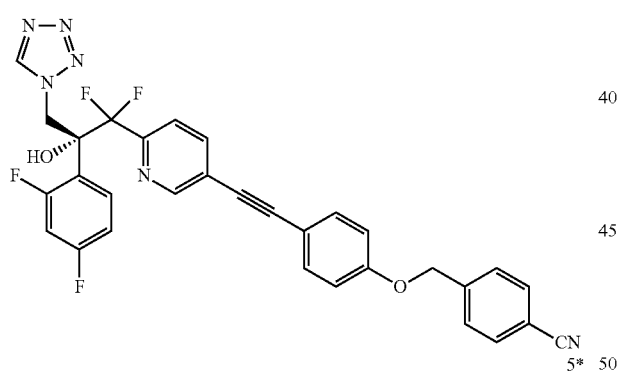

5

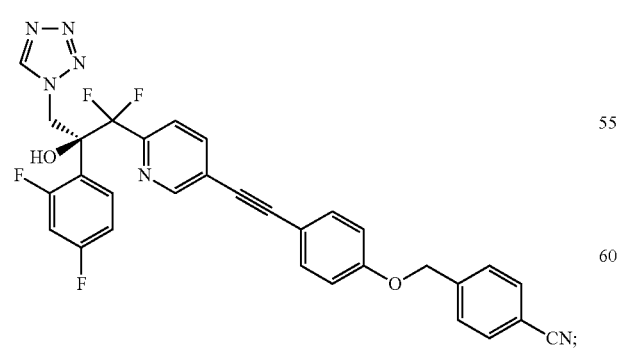

5*

(b) isolating a compound of formula 14 or 14*, or a mixture thereof;

$$Z-\overset{O}{\underset{O}{S}}-OH$$

14* wherein each Z is independently aryl, substituted aryl, alkyl, or substituted alkyl.

12. The process of claim 1, further comprising enriching the enantiomeric purity of an enantiomeric compound mixture of Formula 7 and 7* and/or enriching the enantiomeric purity of an enantiomeric compound mixture of Formula 11 and 11*, comprising:

(i) crystallizing said enantiomeric compound mixture with a chiral acid in a solvent or solvent mixture, wherein:
   the solvent or solvent mixture is selected from acetonitrile, isopropanol, ethanol, water, methanol, or combinations thereof;

(ii) isolating the enantio-enriched chiral salt mixture; and (iii) free-basing the enantio-enriched chiral salt mixture to provide the enantio-enriched compound mixture.

13. The process of claim 12, further comprising reslurrying the enantio-enriched chiral salt mixture in a slurrying solvent or slurrying solvent mixture.

14. The process of claim 12, wherein the solvent or solvent mixture is (a) acetonitrile or (b) a mixture of acetonitrile and isopropanol.

15. The process of claim 13, wherein the slurrying solvent or slurrying solvent mixture is (a) acetonitrile or (b) a mixture of acetonitrile and isopropanol.

16. The process of claim 14, wherein the mixture of acetonitrile and isopropanol comprises 80-90% acetonitrile and 10-20% isopropanol.

17. The process of claim 15, wherein the mixture of acetonitrile and isopropanol comprises 80-90% acetonitrile and 10-20% isopropanol.

18. The process of claim 12, wherein the chiral acid is selected from the group consisting of tartaric acid, dibenzoyltartaric acid, malic acid, camphoric acid, camphorsulfonic acid, ascorbic acid, and di-p-toluoyltartaric acid.

19. The process of claim 13, wherein the chiral acid is selected from the group consisting of tartaric acid, dibenzoyltartaric acid, malic acid, camphoric acid, camphorsulfonic acid, ascorbic acid, and di-p-toluoyltartaric acid.

20. The process of claim 1, wherein the chiral catalyst is

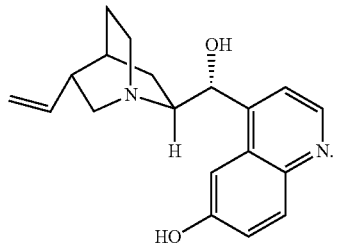 [SMILES: C=CC1CN2CCC1CC2[C@H](O)c1ccnc2ccc(O)cc12]

21. The process of claim 20, wherein the mole percent of the chiral catalyst is 0.5-50.

22. The process of claim 20, wherein the mole percent of the chiral catalyst is 0.5-25.

23. The process of claim 20, wherein the mole percent of the chiral catalyst is 1-10.

24. The process of claim 20, wherein the mole percent of the chiral catalyst is 5.

25. The process of claim 1, wherein the number of equivalents of nitromethane is 1-25.

26. The process of claim 1, wherein the number of equivalents of nitromethane is 5-15.

27. The process of claim 1, wherein the number of equivalents of nitromethane is 10.

* * * * *